United States Patent
Thompson et al.

(10) Patent No.: US 10,384,749 B2
(45) Date of Patent: Aug. 20, 2019

(54) METHOD, APPARATUS AND SYSTEM FOR OBTAINING AND MONITORING ENVIRONMENTAL DATA

(71) Applicant: LOST BIRD PROJECT, INC., New York, NY (US)

(72) Inventors: Benjamin Thompson, San Diego, CA (US); Andrew Stern, Pittsford, NY (US)

(73) Assignee: LOST BIRD PROJECT, INC., New York, NY (US)

( * ) Notice: Subject to any disclaimer, the term of this patent is extended or adjusted under 35 U.S.C. 154(b) by 49 days.

(21) Appl. No.: 15/116,472

(22) PCT Filed: Feb. 4, 2015

(86) PCT No.: PCT/US2015/014454
§ 371 (c)(1),
(2) Date: Aug. 3, 2016

(87) PCT Pub. No.: WO2015/120046
PCT Pub. Date: Aug. 13, 2015

(65) Prior Publication Data
US 2016/0347426 A1    Dec. 1, 2016

Related U.S. Application Data

(60) Provisional application No. 61/935,399, filed on Feb. 4, 2014.

(51) Int. Cl.
*B63B 35/79* (2006.01)
*G01C 13/00* (2006.01)
(Continued)

(52) U.S. Cl.
CPC .......... *B63B 35/7926* (2013.01); *B63B 35/85* (2013.01); *G01C 13/00* (2013.01);
(Continued)

(58) Field of Classification Search
CPC ................ B63B 35/7926; B63B 35/85; B63B 2022/006; B63B 2211/02; H02J 50/10; H02J 7/025; G01C 13/00; H04N 21/42202; G01N 27/414
See application file for complete search history.

(56) References Cited

U.S. PATENT DOCUMENTS

| 5,590,908 A | 1/1997 | Can |
| 7,302,905 B1 | 12/2007 | Wynne |

(Continued)

FOREIGN PATENT DOCUMENTS

| WO | WO 03/056529 A1 | 7/2003 |
| WO | WO 2005/012079 A1 | 2/2005 |

(Continued)

OTHER PUBLICATIONS

International Search Report, PCT/US2015/014454, dated May 11, 2015 (4 pages).

(Continued)

*Primary Examiner* — Mohamed Charioui
*Assistant Examiner* — Jeremy A Delozier
(74) *Attorney, Agent, or Firm* — Polsinelli LLP

(57) ABSTRACT

In at least one aspect, a water-sports board is configured to collect environmental data. The water-sports board includes a waterproof sensor housing and, disposed within the housing, one or more sensor(s), processor(s), memory device(s), switch(es), batteries. The sensing device is configured, in a first state, not to store environmental data sensed by the at least one sensor in the at least one physical memory device. The sensing device is configured, in a second state, to store environmental data sensed by the at least one sensor in the at least one physical memory device.

18 Claims, 18 Drawing Sheets

(51) Int. Cl.
*B63B 35/85* (2006.01)
*H02J 50/10* (2016.01)
*H02J 7/02* (2016.01)
*H04N 21/422* (2011.01)
*G01N 33/18* (2006.01)
*G01N 27/414* (2006.01)
*B63B 22/00* (2006.01)

(52) U.S. Cl.
CPC .............. *G01N 33/18* (2013.01); *H02J 7/025* (2013.01); *H02J 50/10* (2016.02); *H04N 21/42202* (2013.01); *B63B 2022/006* (2013.01); *B63B 2211/02* (2013.01); *G01N 27/414* (2013.01)

(56) References Cited

U.S. PATENT DOCUMENTS

| | | | |
|---|---|---|---|
| 2006/0015287 A1* | 1/2006 | Vock | A42B 3/046 702/141 |
| 2008/0080734 A1 | 4/2008 | Forth | |
| 2011/0056423 A1 | 3/2011 | Railey | |
| 2011/0201238 A1 | 8/2011 | Rott | |
| 2011/0214500 A1* | 9/2011 | Cabrera | G01C 13/00 73/170.29 |
| 2012/0234089 A1 | 9/2012 | Llinas | |
| 2013/0314044 A1 | 11/2013 | Bahadik | |
| 2013/0323989 A1 | 12/2013 | Derrah | |
| 2014/0002239 A1 | 1/2014 | Rayner | |

FOREIGN PATENT DOCUMENTS

| | | |
|---|---|---|
| WO | WO 2013/100228 A1 | 7/2013 |
| WO | WO 2015/120046 A1 | 8/2015 |

OTHER PUBLICATIONS

Written Opinion of the International Searching Authority, PCT/US2015/014454, dated May 11, 2015 (12 pages).

European Patent Office, Extended European Search Report for Application No. EP 15746160, dated Aug. 31, 2017 (9 pages).

* cited by examiner

Status LEDs

Inductive Charging Qi Reciever

| Qty | Value | Device | Package | Parts | Description |
|---|---|---|---|---|---|
| 1 | 2.2nF (50V) | CAP0603-CAP | 0603-CAP | IMU_C2 | Capacitor |
| 1 | 0.1uF | CAP0603-CAP | 0603-CAP | IMU_C1 | Capacitor |
| 7 | 1uF | CAP0603-CAP | 0603-CAP | BB_C1, BT_C1, CPU_C1, C_VBAT, GPS_C1, SD_C1, SNS_C1 | Capacitor |
| 4 | 4.7uF | CAP0603-CAP | 0603-CAP | BB_C2, CHG_C1, GPS_C2, PWR_C1 | Capacitor |
| 1 | 22uF | CAP0603-CAP | 0603-CAP | CPU_C2 | Capacitor |
| 9 | 330 ohm | RESISTOR0603-RES | 0603-RES | BAT_R1, BT_R3, BT_R5, BT_R6, CHG_R1, GPS_R1, GPS_R2, PWR_R1, ST_R1 | Resistor |
| 1 | 1k | RESISTOR0603-RES | 0603-RES | BT_R2 | Resistor |
| 7 | 4.7k | RESISTOR0603-RES | 0603-RES | BAT_R2, BAT_R3, BMON_R1, I2C_R1, I2C_R2, TMP_R1, TMP_R2 | Resistor |
| 5 | 10k | RESISTOR0603-RES | 0603-RES | BMON_R2, BT_R1, CPU_R1, CPU_R2, PINT_R1 | Resistor |
| 7 | 20k | RESISTOR0603-RES | 0603-RES | BB_R1, BB_R2, BMON_R3, BT_R4, GPS_R3, SD_R1, SNS_R1 | Resistor |
| 1 | LTC3240-3.3S | LTC3240-3.3S | 6-DFN | PWR_U1 | Boost/Buck 3.3v regulator |
| 2 | DS18B20 | DS18B20 | 8-USOP | TEMP_1, TEMP_2 | Temperature sensor |
| 2 | RED 1ma | LED0603 | LED-0603 | CHG_LED1, PWR_LED1 | Red LED |
| 2 | GRN 1ma | LED0603 | LED-0603 | BAT_LED, BT_LED1 | Green LED |
| 1 | YEL 1ma | LED0603 | LED-0603 | ST_LED1 | Yellow LED |
| 1 | PTCSMD | PTCSMD | PTC-1206 | F1 | Resettable Fuse PTC |
| 1 | IMU | MPU-9250 | MPU-9250 | IMU | IMU 9-axis sensor |
| 1 | RN42 - Bluetooth Module | RN42 | RN42 | BT | Bluetooth module |
| 1 | MMBT5088 | TRANSISTOR_NPNSOT23-3 | SOT23-3 | PINT_Q1 | Generic NPN BJT SOT-23 case |
| 1 | AH183-WG | AH183-WG | SOT23 | HALL_1 | Hall Device |
| 2 | FDV302P | FDV302P | SOT23-3 | BB_Q1, BMON_Q1 | P-Channel Enhancement MOSFET -200V; -0,15A; 11Ohm |
| 1 | MCP73831 | MCP73831 | SOT23-5 | BAT_CHG | Microchip's MCP73831 |
| 1 | ATXMEGA64D4 | ATXMEGAXX-44PIN | TQFP44 | ATXMEGA | CPU ATMega64D4 |
| 5 | SSM3J328R | SSM3J328R | SOT23-3 | BAT_Q1, Q1, Q2, Q3, Q4 | P-Channel Enh MOSFET SSM3J328R 20V 6A 1.5VGSth |
| 2 | CDBU0530 | CDBU0530 | 0603-DIODE | BAT_D1, BAT_D2 | 0.5A 20V SCHOTTKY BARRIER RECTIFIER |
| 1 | MMSZ4678TP | MMSZ4678TP | SOD123FL | BB_D1 | Reference DIODE |
| 1 | UC530_GPS | UC530_GPS | FASTRAX_UC530C4322 | GPS | Fastrax UC530 GPS Module |
| 1 | MICROSD-SOCKET | MICROSD-SOCKET | MOLEX-104031-0811 | SD1 | MicroSD card socket with card detect |

FIG. 5A

| Item # | Qty | RefDes | Part No. | Description | Package | Type |
|---|---|---|---|---|---|---|
| 1 | 1 | IMU_C2 | 399-1085-1-ND | CAP 2.2nF (50V) | 0603-CAP | smt |
| 2 | 1 | IMU_C1 | 445-5666-1-ND | CAP 0.1uF | 0603-CAP | smt |
| 3 | 7 | BB_C1, BT_C1, CPU_C1, C_VBAT, GPS_C1, SD_C1, SNS_C1 | 445-13234-1-ND | CAP 1uF | 0603-CAP | smt |
| 4 | 4 | BB_C2, CHG_C1, GPS_C2, PWR_C1 | 445-11253-1-ND | CAP 4.7uF | 0603-CAP | smt |
| 5 | 1 | CPU_C2 | 445-8028-1-ND | CAP 22uF | 0603-CAP | smt |
| 6 | 9 | BAT_R1, BT_R3, BT_R5, BT_R6, CHG_R1, GPS_R1, GPS_R2, PWR_R1, ST_R1 | 541-330GCT-ND | RES 330 ohm | 0603-RES | smt |
| 7 | 1 | BT_R2 | A106049CT-ND | RES 1k | 0603-RES | smt |
| 8 | 7 | BAT_R2, BAT_R3, BMON_R1, I2C_R1, I2C_R2, TMP_R1, TMP_R2 | 541-4.7KGCT-ND | RES 4.7k | 0603-RES | smt |
| 9 | 5 | BMON_R2, BT_R1, CPU_R1, CPU_R2, PINT_R1 | 541-10KGCT-ND | RES 10k | 0603-RES | smt |
| 10 | 7 | BB_R1, BB_R2, BMON_R3, BT_R4, GPS_R3, SD_R1, SNS_R1 | A102237CT-ND | RES 20k | 0603-RES | smt |
| 11 | 1 | PWR_U1 | LTC3240EDC-3.3#TRMPBFCT-ND | LTC3240-3.3S | 6-DFN | Fine-pitch |
| 12 | 2 | TEMP_1, TEMP_2 | DS18B20U+T&RCT-ND | DS18B20 | 8-USOP | smt |
| 13 | 2 | CHG_LED1, PWR_LED1 | 754-1122-1-ND | LED RED 1ma | LED-0603 | smt |
| 14 | 2 | BAT_LED, BT_LED1 | 754-1121-1-ND | LED GRN 1ma | LED-0603 | smt |
| 15 | 1 | ST_LED1 | 754-1124-1-ND | LED YEL 1ma | LED-0603 | smt |
| 16 | 1 | F1 | F3370CT-ND | PTCSMD | PTC-1206 | smt |
| 17 | 1 | IMU | 1428-1019-1-ND | MPU-9250 IMU | MPU-9250 | Fine-pitch |
| 18 | 1 | BT | 740-1038-ND | RN42 - Bluetooth Module | RN42 | smt |
| 19 | 1 | PINT_Q1 | MMBT5088CT-ND | MMBT5088 | SOT23-3 | smt |
| 20 | 1 | HALL_1 | AH183-WG-7DICT-ND | AH183-WG | SOT23 | smt |
| 21 | 2 | BB_Q1, BMON_Q1 | FDV302PCT-ND | FDV302P | SOT23-3 | smt |
| 22 | 1 | BAT_CHG | MCP73831T-2ACI/OTCT-ND | MCP73831 | SOT23-5 | smt |
| 23 | 1 | ATXMEGA | ATXMEGA64D4-AU-ND | ATXMEGA64D4 | TQFP44 | smt |
| 24 | 5 | BAT_Q1, Q1, Q2, Q3, Q4 | SSM3J328RLF(TCT-ND | SSM3J328R | SOT23-3 | smt |
| 25 | 2 | BAT_D1, BAT_D2 | 641-1285-1-ND | CDBU0530 | 0603-DIODE | smt |
| 26 | 1 | BB_D1 | MMSZ4678-TPMSCT-ND | MMSZ4678TP | SOD123FL | smt |
| 27 | 1 | GPS | MOUSER: 916-UC530 | UC530_GPS | FASTRAX_UC530C4322 | smt |
| 28 | 1 | SD1 | MOUSER: 538-104031-0811 | MICROSD-SOCKET | MOLEX-104031-0811 | smt |

FIG. 5B

| Qty | Value | Device | Package | Parts | Description |
|---|---|---|---|---|---|
| 1 | 2.2nF (50V) | CAP0603-CAP | 0603-CAP | IMU_C2 | Capacitor |
| 2 | 0.01uF | CAP0603-CAP | 0603-CAP | C_BOOT1, C_BOOT2 | Capacitor |
| 2 | 47nF | CAP0603-CAP | 0603-CAP | C_COMM1, C_COMM2 | Capacitor |
| 1 | 0.1uF | CAP0603-CAP | 0603-CAP | IMU_C1 | Capacitor |
| 1 | 0.12uF | CAP0603-CAP | 0603-CAP | QI_C2 | Capacitor |
| 3 | 0.47uF | CAP0603-CAP | 0603-CAP | C_CLAMP1, C_CLAMP2, QI_C1 | Capacitor |
| 7 | 1uF | CAP0603-CAP | 0603-CAP | BB_C1, BT_C1, CPU_C1, C_VBAT, GPS_C1, SD_C1, SNS_C1 | Capacitor |
| 4 | 4.7uF | CAP0603-CAP | 0603-CAP | BB_C2, GPS_C2, PWR_C1, QI_C4 | Capacitor |
| 1 | 10uF | CAP0603-CAP | 0603-CAP | QI_C3 | Capacitor |
| 1 | 22uF | CAP0603-CAP | 0603-CAP | CPU_C2 | Capacitor |
| 1 | 187 ohm | RESISTOR0603-RES | 0603-RES | R_FOD | Resistor |
| 10 | 330 ohm | RESISTOR0603-RES | 0603-RES | BAT_R1, BT_R3, BT_R5, BT_R6, GPS_R1, GPS_R2, PWR_R1, QI_R1, R_ILIM, ST_R1 | Resistor |
| 2 | 1k | RESISTOR0603-RES | 0603-RES | BT_R2, ROS1 | Resistor |
| 7 | 4.7k | RESISTOR0603-RES | 0603-RES | BAT_R2, BAT_R3, BMON_R1, I2C_R1, I2C_R2, TMP_R1, TMP_R2 | Resistor |
| 6 | 10k | RESISTOR0603-RES | 0603-RES | BMON_R2, BT_R1, CPU_R1, CPU_R2, PINT_R1, R_CTRL | Resistor |
| 7 | 20k | RESISTOR0603-RES | 0603-RES | BB_R1, BB_R2, BMON_R3, BT_R4, GPS_R3, SD_R1, SNS_R1 | Resistor |
| 1 | LTC3240-3.3S | LTC3240-3.3S | 6-DFN | PWR_U1 | Boost/Buck 3.3v regulator |
| 1 | DS18B20 | DS18B20 | 8-USOP | TEMP_1, TEMP_2 | Temperature Sensor |
| 2 | RED 1ma | LED0603 | LED-0603 | PWR_LED1, QI_LED1 | Red LED |
| 2 | GRN 1ma | LED0603 | LED-0603 | BAT_LED, BT_LED1 | Green LED |
| 2 | YEL 1ma | LED0603 | LED-0603 | ST_LED1 | Yellow LED |
| 1 | PTCSMD | PTCSMD | PTC-1206 | F1 | Resettable Fuse PTC |
| 1 | IMU | MPU-9250 | MPU-9250 | IMU | IMU 9-axis sensor |
| 1 | BQ51013B | BQ51013B | R-PVQFN-N20 | QI_U1 | QI Receiver |
| 1 | RN42 - Bluetooth Module | RN42 | RN42 | BT | Bluetooth Module |
| 1 | MMBT5088 | TRANSISTOR_NPNSOT23-3 | SOT23-3 | PINT_Q1 | Generic NPN BJT SOT-23 case |
| 1 | SS351AT | SS351AT | SOT23 | HALL_1 | Hall Device |
| 2 | FDV302P | FDV302P | SOT23-3 | BB_Q1, BMON_Q1 | P-Channel Enhancement MOSFET -200V; -0.15A; 11Ohm |
| 1 | MCP73831 | MCP73831 | SOT23-5 | BAT_CHG | Microchip's MCP73831 |
| 1 | ATXMEGA64D4 | ATXMEGAXX-44PIN | TQFP44 | ATXMEGA | CPU ATXMega64D4 |
| 5 | SSM3J328R | SSM3J328R | SOT23-3 | BAT_Q1, Q1, Q2, Q3, Q4 | P-Channel Enh MOSFET SSM3J328R 20V 6A 1.5VGSth |
| 2 | CDBU0530 | CDBU0530 | 0603-DIODE | BAT_D1, BAT_D2 | 0.5A 20V SCHOTTKY BARRIER RECTIFIER |
| 1 | MMSZ4678TP | MMSZ4678TP | SOD123FL | BB_D1 | Reference DIODE |
| 1 | UC530_GPS | UC530_GPS | FASTRAX_UC530C43£GPS | FASTRAX-104031-0811 | Fastrax UC530 GPS Module |
| 1 | MICROSD-SOCKET | MICROSD-SOCKET | MOLEX-104031-0811 | SD1 | MicroSD card socket with card detect |

FIG. 5C

| Item # | Qty | RefDes | Part No. | Description | Package | Type |
|---|---|---|---|---|---|---|
| 1 | 1 IMU_C2 | | 399-1085-1-ND | CAP 2.2nF (50V) | 0603-CAP | smt |
| 2 | 2 C_BOOT1, C_BOOT2 | | 445-5100-1-ND | CAP 0.01uF | 0603-CAP | smt |
| 3 | 2 C_COMM1, C_COMM2 | | 445-8127-1-ND | CAP 47nF | 0603-CAP | smt |
| 4 | 1 IMU_C1 | | 445-5666-1-ND | CAP 0.1uF | 0603-CAP | smt |
| 5 | 1 QI_C2 | | 490-6430-1-ND | CAP 0.12uF | 0603-CAP | smt |
| 6 | 3 C_CLAMP1, C_CLAMP2, QI_C1 | | 445-5144-1-ND | CAP 0.47uF | 0603-CAP | smt |
| 7 | 7 BB_C1, BT_C1, CPU_C1, C_VBAT, GPS_C1, SD_C1, SNS_C1 | | 445-13234-1-ND | CAP 1uF | 0603-CAP | smt |
| 8 | 4 BB_C2, GPS_C2, PWR_C1, QI_C4 | | 445-11253-1-ND | CAP 4.7uF | 0603-CAP | smt |
| 9 | 1 QI_C3 | | 1276-1869-1-ND | CAP 10uF | 0603-CAP | smt |
| 10 | 1 CPU_C2 | | 445-8028-1-ND | CAP 22uF | 0603-CAP | smt |
| 11 | 1 R_FOD | | 541-187HCT-ND | RES 187 ohm | 0603-RES | smt |
| 12 | 10 BAT_R1, BT_R3, BT_R5, BT_R6, GPS_R1, GPS_R2, PWR_R1, QI_R1, R_ILIM, ST_R1 | | 541-330GCT-ND | RES 330 ohm | 0603-RES | smt |
| 13 | 2 BT_R2, ROS1 | | A106049CT-ND | RES 1k | 0603-RES | smt |
| 14 | 7 BAT_R2, BAT_R3, BMON_R1, I2C_R1, I2C_R2, TMP_R1, TMP_R2 | | 541-4.7KGCT-ND | RES 4.7k | 0603-RES | smt |
| 15 | 6 BMON_R2, BT_R1, CPU_R1, CPU_R2, PINT_R1, R_CTRL | | 541-10KGCT-ND | RES 10k | 0603-RES | smt |
| 16 | 7 BB_R1, BB_R2, BMON_R3, BT_R4, GPS_R3, SD_R1, SNS_R1 | | A102237CT-ND | RES 20k | 0603-RES | smt |
| 17 | 1 PWR_U1 | | LTC3240EDC-3.3#TRMPBFCT-ND | LTC3240-3.3S | 6-DFN | Fine-pitch |
| 18 | 2 TEMP_1, TEMP_2 | | DS18B20U+T&RCT-ND | DS18B20 | 8-USOP | smt |
| 19 | 2 PWR_LED1, QI_LED1 | | 754-1122-1-ND | RED 1ma | LED-0603 | smt |
| 20 | 2 BAT_LED, BT_LED1 | | 754-1121-1-ND | GRN 1ma | LED-0603 | smt |
| 21 | 1 ST_LED1 | | 754-1124-1-ND | YEL 1ma | LED-0603 | smt |
| 22 | 1 F1 | | F3370CT-ND | PTCSMD | PTC-1206 | smt |
| 23 | 1 IMU | | 1428-1019-1-ND | IMU | MPU-9250 | Fine-pitch |
| 24 | 1 QI_U1 | | 296-35638-1-ND | BQ51013B | R-PVQFN-N20 | Fine-pitch |
| 25 | 1 BT | | 740-1038-ND | RN42 - Bluetooth Module | RN42 | smt |
| 26 | 1 PINT_Q1 | | MMBT5088CT-ND | MMBT5088 | SOT23-3 | smt |
| 27 | 1 HALL_1 | | 480-3610-1-ND | SS351AT | SOT23 | smt |
| 28 | 2 BB_Q1, BMON_Q1 | | FDV302PCT-ND | FDV302P | SOT23-3 | smt |
| 29 | 1 BAT_CHG | | MCP73831T-2ACI/OTCT-ND | MCP73831 | SOT23-5 | smt |
| 30 | 1 ATXMEGA | | ATXMEGA64D4-AU-ND | ATXMEGA64D4 | TQFP44 | smt |
| 31 | 5 BAT_Q1, Q1, Q2, Q3, Q4 | | SSM3J328RLF(TCT-ND | SSM3J328R | SOT23-3 | smt |
| 32 | 2 BAT_D1, BAT_D2 | | 641-1285-1-ND | CDBU0530 | 0603-DIODE | smt |
| 33 | 1 BB_D1 | | MMSZ4678-TPMSCT-ND | MMSZ4678TP | SOD123FL | smt |
| 34 | 1 GPS | | MOUSER: 916-UC530 | UC530_GPS | FASTRAX_UC530C4322 | smt |
| 35 | 1 SD1 | | MOUSER: 538-104031-0811 | MICROSD-SOCKET | MOLEX-104031-0811 | smt |

FIG. 5D

METHOD, APPARATUS AND SYSTEM FOR OBTAINING AND MONITORING ENVIRONMENTAL DATA

CROSS-REFERENCE TO RELATED APPLICATIONS

This application is a U.S. National Stage of International Application No. PCT/US2015/014454, filed Feb. 4, 2015, which claims priority to and the benefits of U.S. Patent Application No. 61/935,399, filed Feb. 4, 2014, the disclosures of which are each hereby incorporated by reference herein in their entireties.

TECHNICAL FIELD

The embodiments of the invention are related to systems and methods for obtaining environmental data and for monitoring of such environmental data.

BACKGROUND

Buoys that collect oceanographic and atmospheric data ("weather buoys") are currently deployed, either moored or drifting, throughout the world's oceans and bodies of water. Weather buoys collect various data such as wind velocity (steady and gusting), wind direction, barometric pressure, water temperature, water currents, wave height, and wave direction.

Deploying and maintaining buoys in the ocean is laborious and expensive. The ocean is also a hostile dynamic environment, with moored weather buoys going adrift and with moored and drifting weather buoys being damaged or broken. Because of these challenges, there are a limited number of weather buoys in the world. Furthermore, very few weather buoys or other monitoring systems are deployed in the nearshore environment (within 400 meters of the shore). Waves crest and break in the nearshore environment and, because of this water movement, the bathymetry is also changing. For these reasons, there are very few nearshore environmental monitoring systems maintained around the world.

SUMMARY OF THE INVENTION

In one aspect of the present concepts, a water-sports board comprises a sensing device configured to collect environmental data, the sensing device comprising at least one waterproof sensor housing, at least one sensor disposed within the at least one sensor housing, at least one processor disposed within the at least one sensor housing, the at least one processor being communicatively connected to the at least one sensor, and at least one physical memory device disposed within the at least one sensor housing, the at least one memory physical device being communicatively connected with the at least one processor. The sensing device further comprises at least one switch adapted to change a state of the sensing device between at least a first state and a second state and at least one battery configured to power at least one of the at least sensor, the at least one processor, or the at least one memory device. The sensing device is configured, in the first state, not to store environmental data sensed by the at least one sensor in the at least one physical memory device, and is configured, in the second state, to store environmental data sensed by the at least one sensor in the at least one physical memory device.

In at least some other aspects, the present concepts include a waterproof device configured to collect environmental data, the device comprising at least one waterproof sensor housing integrated with a device borne by a person or attached to a device borne by a person. At least one sensor and at least one processor are disposed within the at least one sensor housing, the at least one processor being communicatively connected to the at least one sensor. Also disposed within the at least one sensor housing is at least one physical memory device, the at least one memory physical device being communicatively connected with the at least one processor and at least one switch adapted to change a state of the at least one sensor between at least a first state and a second state responsive to a manual manipulation of the at least one switch, automatically responsive to at least one triggering event, or either of a manual manipulation of the at least one switch through the at least one waterproof sensor or automatically responsive to at least one triggering event. The device further comprises at least one battery configured to power at least one of the at least one sensor, the at least one processor, or the at least one memory device. The first state is an off state and the second state is an on state. While in the second state, data sensed by the at least one sensor is stored in the at least one physical memory device.

In still another aspect of the present concepts, a method for collecting environmental data, comprises the acts of integrating a waterproof environmental data sensing device comprising one or more sensors, at least one processor, at least one battery and at least one physical memory device into water-sports equipment adapted for use in a water-sports activity and activating the environmental data sensing device prior to or during initiation of the water-sports activity to enable collection of environmental data during the water-sports activity. The method further includes the acts of collecting environmental data using the one or more sensors during the water-sports activity and transmitting the environmental data to a central server via at least one communication device, wherein the environmental data comprises at least one of a water temperature, a water salinity, a water conductivity, a water pH, or any combination thereof.

Additional aspects of the invention will be apparent to those of ordinary skill in the art in view of the detailed description of various embodiments, which is made with reference to the drawings, a brief description of which is provided below.

BRIEF DESCRIPTION OF THE DRAWINGS

FIGS. 5(A)-5(B) are a listing of components of the sensing device circuitry in FIGS. 4(A)-4(C), and 4(E)-4(K), which use a Qi receiver module. FIGS. 5(C)-5(D) are a listing of components of the sensing device circuitry in FIGS. 4(A)-4(J), which includes a discrete Qi receiver on-board.

Figure 1:
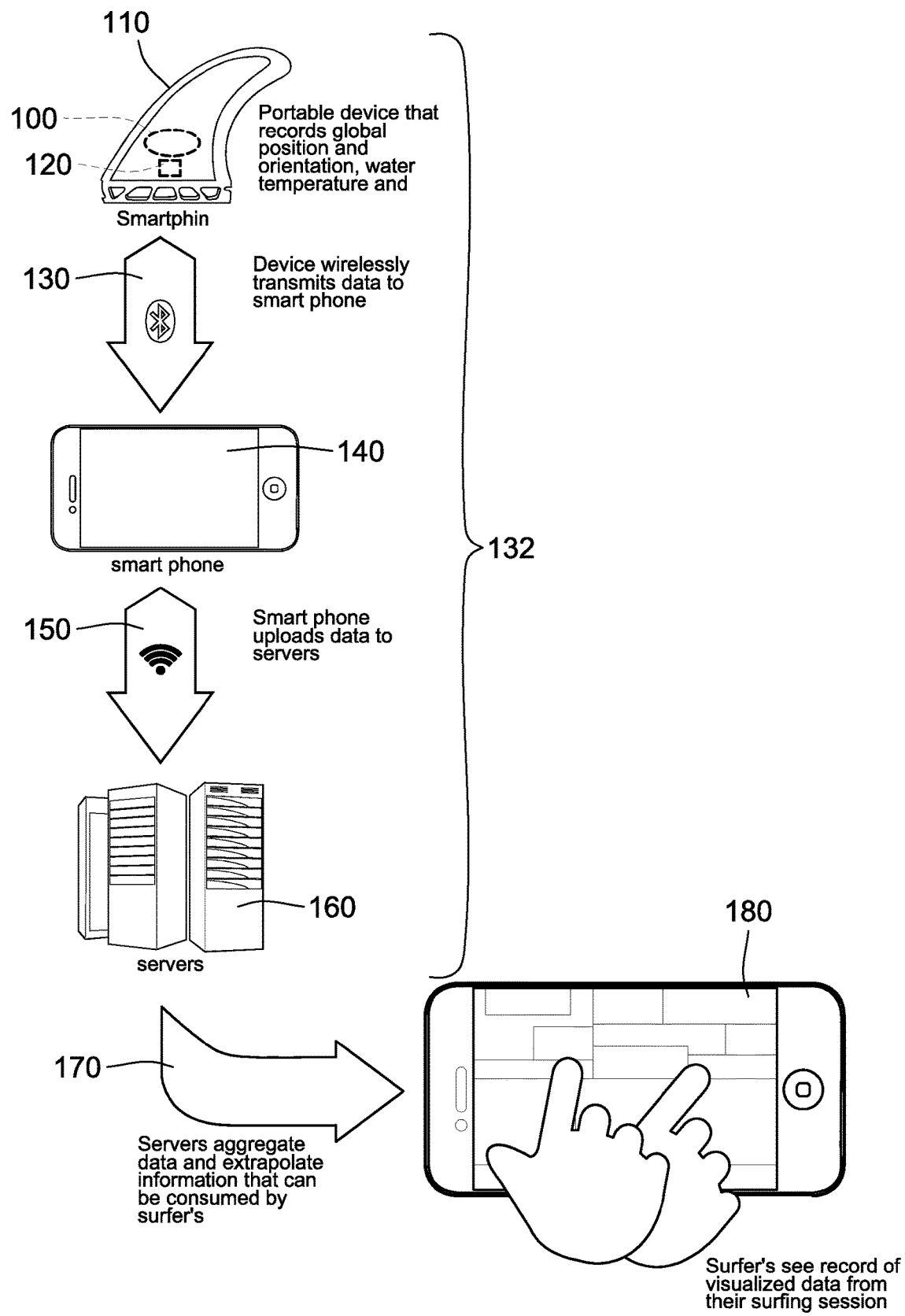
FIG. 1 is a schematic representation of a system for collecting environmental data according to at least some aspects of the present concepts.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION OF THE INVENTION

While this invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated. For purposes of the present detailed description, the singular includes the plural and vice versa (unless specifically disclaimed); the words "and" and "or" shall be both conjunctive and disjunctive; the word "all" means "any and all"; the word "any" means "any and all"; and the word "including" means "including without limitation.

The inventors have developed a system and method to use the practitioners of various water-based activities (e.g., sports such as surfing, etc.) in nearshore environments to deploy sensors that collect data about the natural nearshore environments, and more particularly to incorporate into such water-based activities suitable methods, apparatus and systems for obtaining and monitoring environmental data. In the aggregate, the environmental data can supplement data from conventional methods, apparatus and systems for obtaining and monitoring environmental data (e.g., weather buoys).

The inventors, recognizing the need to raise the public's awareness of the environment, and further recognizing the nexus between all biological systems on the planet and the oceans, developed the present concepts to not only facilitate tracking of oceanographic and atmospheric data, an important goal in its own right, but also to strengthen the public's connection with the oceans by empowering the public to participate in understanding of the nearshore environment, but also to help document and track changes in the nearshore environment over time.

As described herein, surfers, for example, can play an integral role in developing awareness of the nearshore environment and of changes to the nearshore environment over time. In accord with at least some aspects of the present concepts, a surfer's surfboard can be equipped with a sensing device comprising one or more sensors providing data for one or more variables (e.g., variables measured by a conventional weather buoy). In accord with at least some other aspects of the present concepts, a surfer's surfboard can be equipped with a plurality of sensing devices, each of the plurality of sensing devices comprising one or more sensors providing data for one or more variables (e.g., variables measured by a conventional weather buoy). Using such instrumented surfboards, when surfers go into the ocean, the surfboards can record data such as, but not limited to, wave energy, water temperature, water pH, and/or salinity. By various means, this data can then be aggregated and used to describe changes the nearshore environment. In this example, surfers become major stakeholders in the collection of data useful in characterizing the nearshore environment and useful in assessing changes in and any potential trends in such nearshore environment. In at least some aspects, it is desirable, but not necessary, for the device to also collect personal data about the movement of the surfer in the water to encourage utilization of the device, as surfers are more likely to bring the device in the ocean if it can be used to increase the enjoyment of their selected leisure and sport activity. Furthermore, the data about a surfer's movement can be related to the environmental data that the device is monitoring. A surfer will better understand how the environment directly affects his/her experience, which will enhance the surfer's connection with the ocean. Likewise, these same concepts are adaptable to other water-borne activities and other water-based activities can also advantageously utilize one or more sensing devices, each of the one or more sensing devices comprising one or more sensors providing data for one or more variables (e.g., variables measured by a conventional weather buoy). Without limitation, and by way of example, such device(s) as are disclosed herein may be adapted for use by skin divers, scuba divers, wind surfers, ocean kayakers, or other operators of personal watercraft, and may be attached to ones' body and/or ones' equipment (e.g., directly or by a tethered attachment), so long as the device(s) and sensor(s) are positioned to obtain data that is not subjected to untoward measurement biases.

In at least some aspects of the present concepts, a water-sports board (e.g., a surfboard, paddle board, skimboard, body board, windsurfing board, etc.) comprises one or more sensing device(s) 100 configured to collect environmental data. As shown in FIG. 1, a sensing device 100 is disposed in, or integrated with, a fin 110, such as a fin (also referred to herein as a "Smartfin" or "Smartphin") that would be disposed on the ventral side of a surfboard (not shown). Alternatively, in other aspects, the sensing device 100 could be disposed in, or integrated with, the water-sports board itself, such as by being installed, or removably installed, within one or more openings, depressions, or cavities formed in a ventral surface of the water-sports board.

The sensing device 100 comprises one or more sensors disposed in one or more housings, which are advantageously, but not necessarily, waterproof, with the exception of pH and salinity sensors which must be partially exposed to the water to facilitate measurement. The sensor housings are only required to be waterproof where the sensor itself, and any appurtenant components (e.g., processor(s), wiring, memory, etc.) are not themselves waterproofed, and in a manner that does not interfere with components that must be exposed to ocean water. It is envisioned that, in various aspects of the present concepts, the sensing device housing(s) will be waterproof in an assembled, operational condition for use in the water-sports activity and, when not in an operational condition for use in the water-sports activity, the sensing device housing(s) may be opened (e.g., via rotation of a threaded connection cap, unlatching of a gasketed compartment, removal of one or more mechanical connectors to access a sealed interior compartment, etc.) to permit access to one or more components associated with the sensing device 100 such as, but not limited to a removal of a device therein, such as a removable memory device, or to an I/O port (e.g., USB, micro USB, serial, IEEE 1394, IEEE 1394b, HDMI Micro, IrDA, etc.).

The sensing device housing(s) may comprise a single, centralized sensor housing having one or more sensors disposed therein, or may comprise a distributed sensing device comprising a plurality of sensors. By way of example, in a surfboard configuration, a first waterproof sensor housing could be disposed in a first ventral fin and a second waterproof sensor housing could be disposed in a second ventral fin, with each of the first and second waterproof sensor housing bearing the same sensors or different sensors. As another example, also relative to the surfboard configuration, a first waterproof sensor housing could be disposed in a ventral fin at a tail of the surfboard a second waterproof sensor housing could be disposed in, or removably attached to, a ventral surface of the surfboard (e.g., toward a nose of the surfboard or in the vicinity of a midpoint of the surfboard lengthwise and widthwise, etc.). Of course, to the extent that an individual sensor is, itself, waterproofed, thus obviating at least some reasons for utilizing a distinct housing, such sensor may be deployed (e.g., on the surfboard) without a housing.

In various aspects, the sensing device(s) 100 may be integrated into an "after market" modification to existing water-sports equipment or water-borne vessels, where an existing component (e.g., tail fin) is replaced by a corresponding component (e.g., another tail fin) comprising the sensing device(s). In other aspects, the sensing device(s) 100 may be integrated into an OEM product. For example, the sensing device(s) 100 may be integrated into a Hobie paddleboard (e.g., in the paddleboard, in the fin, etc.), surfboard (e.g., in the surfboard, in the fin, etc.), or sailboat (e.g., in the hull, in the rudder, etc.).

In general, the waterproof sensor housing is desired to endure impacts common to the activity in a manner that provides longevity to the sensing device(s) 100 and components housed therein. In the embodiment depicted in FIG. 1, the waterproof housing comprises a fiberglass fin that can be mounted on a ventral surface of a surfboard or other water-sports board. Ideally, the housing material(s) should not markedly interfere with the reception of or transmission of signals (e.g., radio signals) or effect the accuracy of any measurements taken by the sensing device(s) 100.

The sensing device(s) 100 further comprise a CPU (i.e., one or more centralized or distributed processors or processing devices), such as, but not limited to, AVR or ARM processors, disposed within the sensing device housing(s). In other aspects, Qualcomm Snapdragon 200, 400, 600 and 800, Nvidia Tegra 4 and Tegra 4i, Intel Atom Z2580 Clover Trail+, Apple A7, Motorola X8, MediaTek MT6592, Intel Atom Z2420 Lexington, etc., or the like, could be used. The processor(s) are communicatively connected to the sensor(s) and to one or more physical, non-transient memory devices (e.g., non-volatile memory device, solid-state/semiconductor-based flash memory, etc.). The sensing device(s) 100 are power by one or more batteries configured to power all components of the sensing device(s) requiring power to operate (e.g., sensor(s), processor(s), memory device(s), etc.). The battery or batteries are desirably, but not necessarily, rechargeable, either via a charging port or device integrated into the sensing device(s) 100, or following removal of the battery or batteries from the sensing device(s) 100. In at least some aspects, the battery or batteries are configured to be recharged inductively, such as via the Qi inductive power standard. In at least some aspects, the charging port or charging system provides inputs (e.g., instructions, handshake signals, etc.) to the sensing device(s) processor(s) to register the connection of the rechargeable battery to a power charging source and, responsive thereto, the processor(s) are configured to automatically communicatively allow connection from an external communication device (e.g., external device 140 in FIG. 1) that would initiate data transfer from the memory device (e.g., wireless transmission of data 130 to smart phone 140 in FIG. 1). In other aspects of the present concepts, the download or transmission of data from the memory device(s) of the sensing device(s) 100 is initiated manually by a user.

In any event, it is generally desired that the battery or batteries are sized and selected to provide power to all powered elements for between about 2 hours to 8 hours (e.g., between about 2-3 hours or 6-8 hours), or optionally more, to permit sufficient utilization during a desired water-sports activity. In at least some aspects, the sensing device(s) 100 battery or batteries could be sized in correspondence with the water-sports activity and/or anticipated usage (e.g., a first sensing device 100 battery pack could provide a 2-3 hour charge, whereas a second sensing device battery pack could provide a 6-8 hour charge). In at least some aspects, it is desired for the battery or batteries to provide at least about 120 maH (e.g., 3.7V LiPo 120 mAh).

In at least some aspects of the present concepts, the sensing device(s) 100 further comprise one or more switches adapted to change a state of the sensing device(s) 100 between at least a first state and a second state. The sensing device(s) 100 is configured, in the first state, not to store environmental data sensed by the sensor(s) in the memory device(s) and is configured, in the second state, to store environmental data sensed by the sensor(s) in the device(s). Accordingly, when the water-sports board or object bearing the sensing device(s) 100 is not deployed in an intended water-sports activity (e.g., at home, strapped to a car, sitting on the beach, etc.), the sensing devices are inactive not only to minimize discharge of the battery or batteries, but also to prevent the collection of irrelevant or inappropriate data. In at least some aspects, these switches may be manual, user-actuated switches (e.g., one or more user-interfaces including, but not limited to, one or more actuatable buttons, a touch pad, or a connected electronic device such as a smart phone connected to the device via a wireless connection). In at least some other aspects, the switches comprise controller-based switches operating responsive to sensor data received by the controller from one or more sensors and instruction sets stored in the physical, non-transient memory device(s).

Figure 4A:
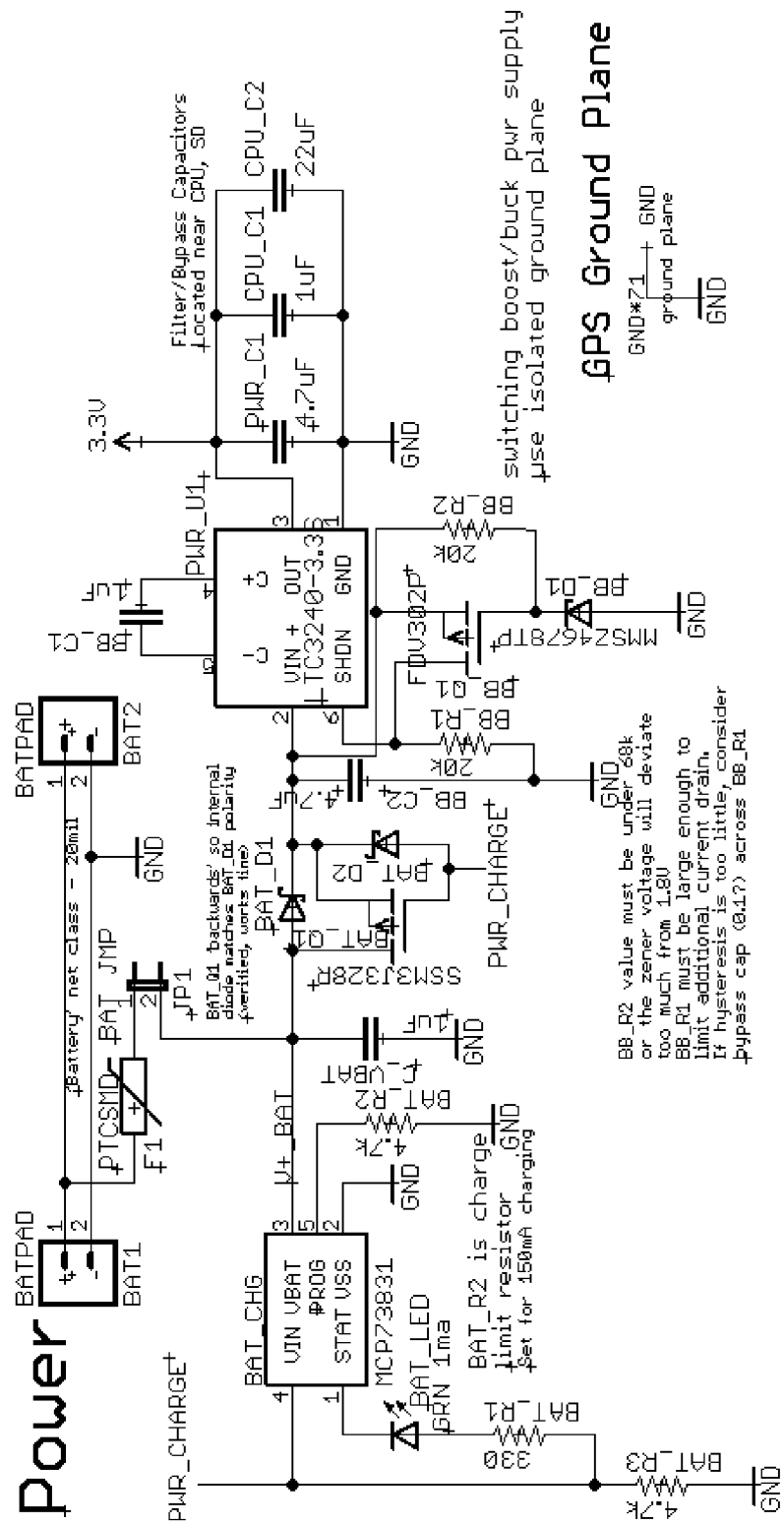
FIGS. 4(A)-4(K) show aspects of sensing device circuitry in accord with at least some aspects of the present concepts. 4(K) is an alternate to 4(D) using a Qi receiver module in lieu of a discrete Qi receiver.
Figure 4B:
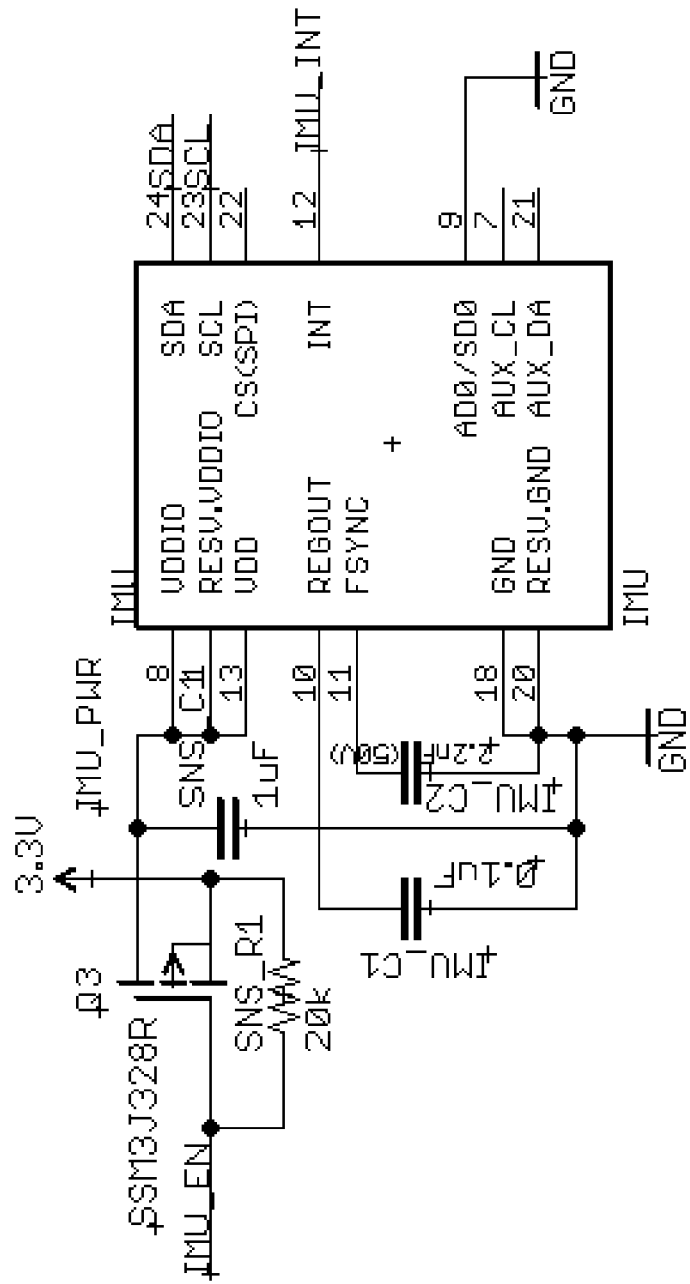
Figure 4C:
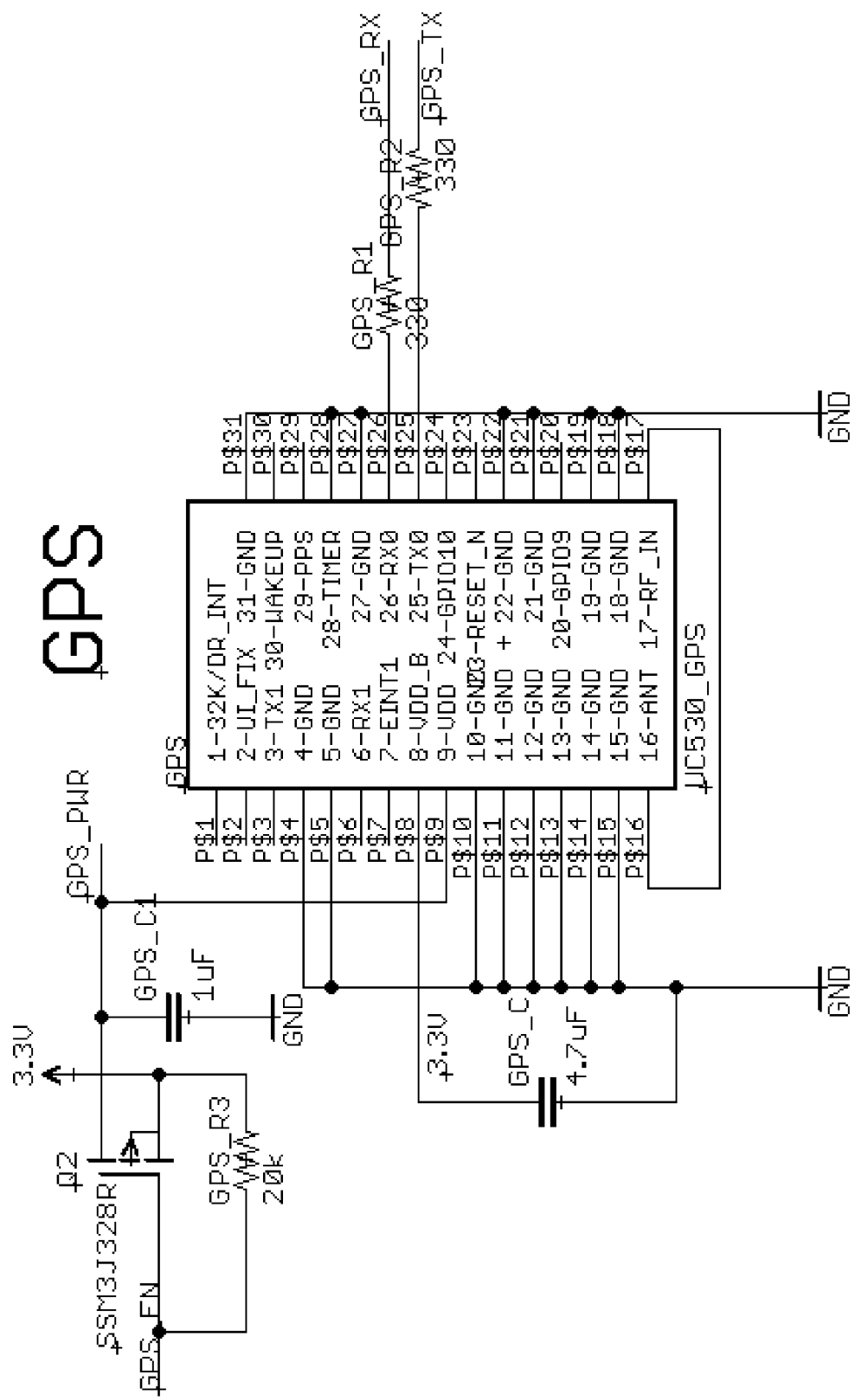
Figure 4D:
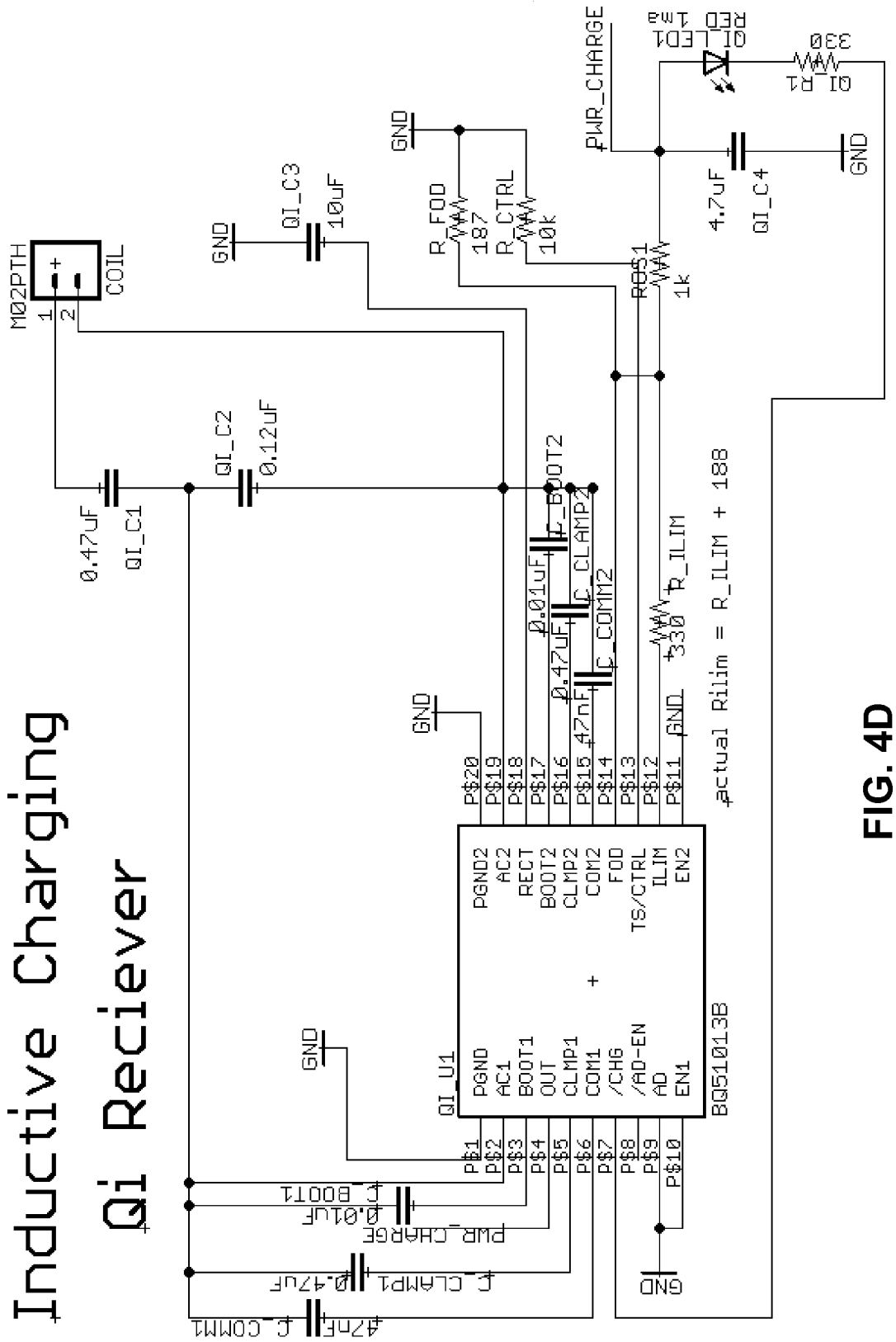
Figure 4E:
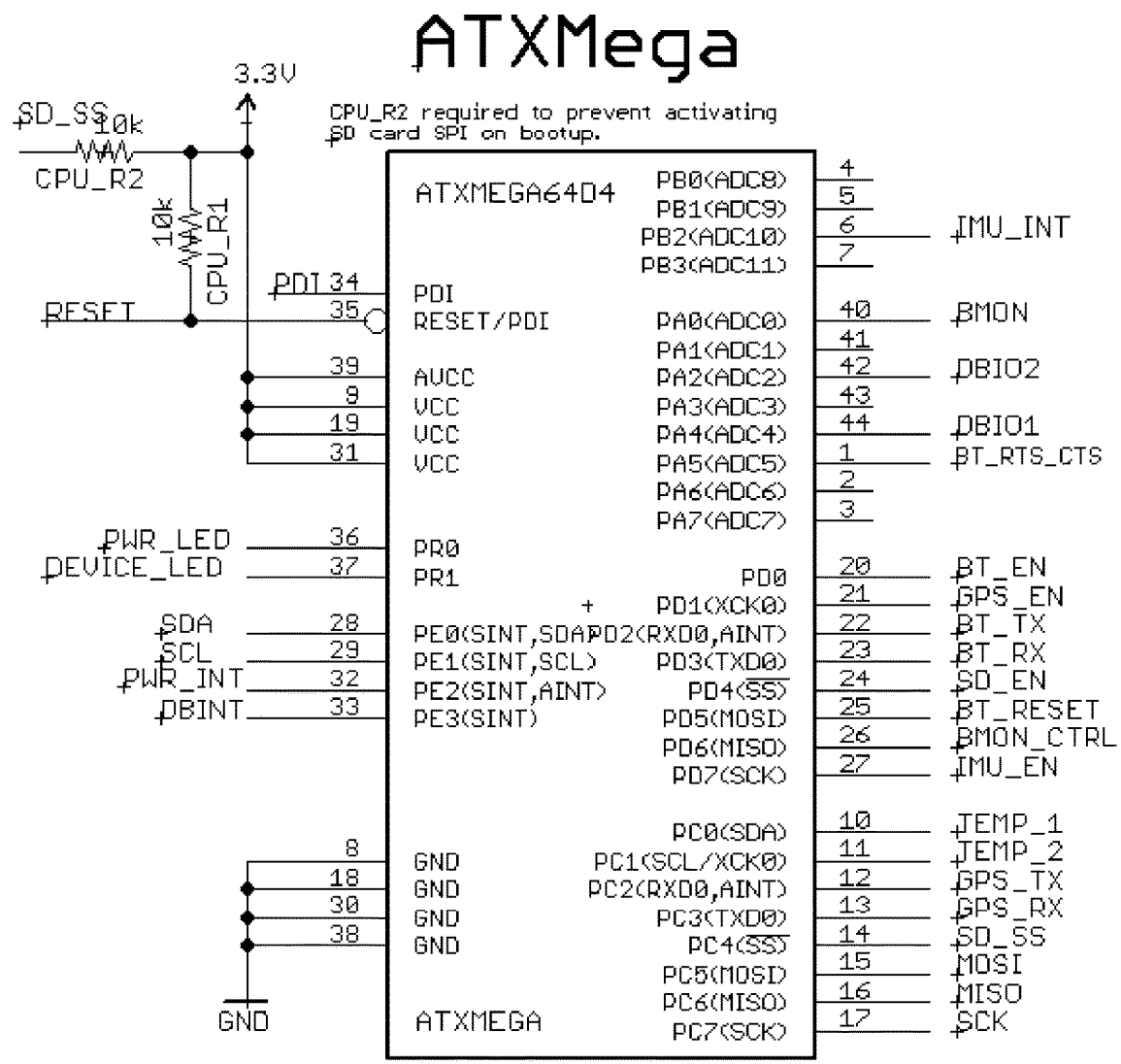
Figure 4F:
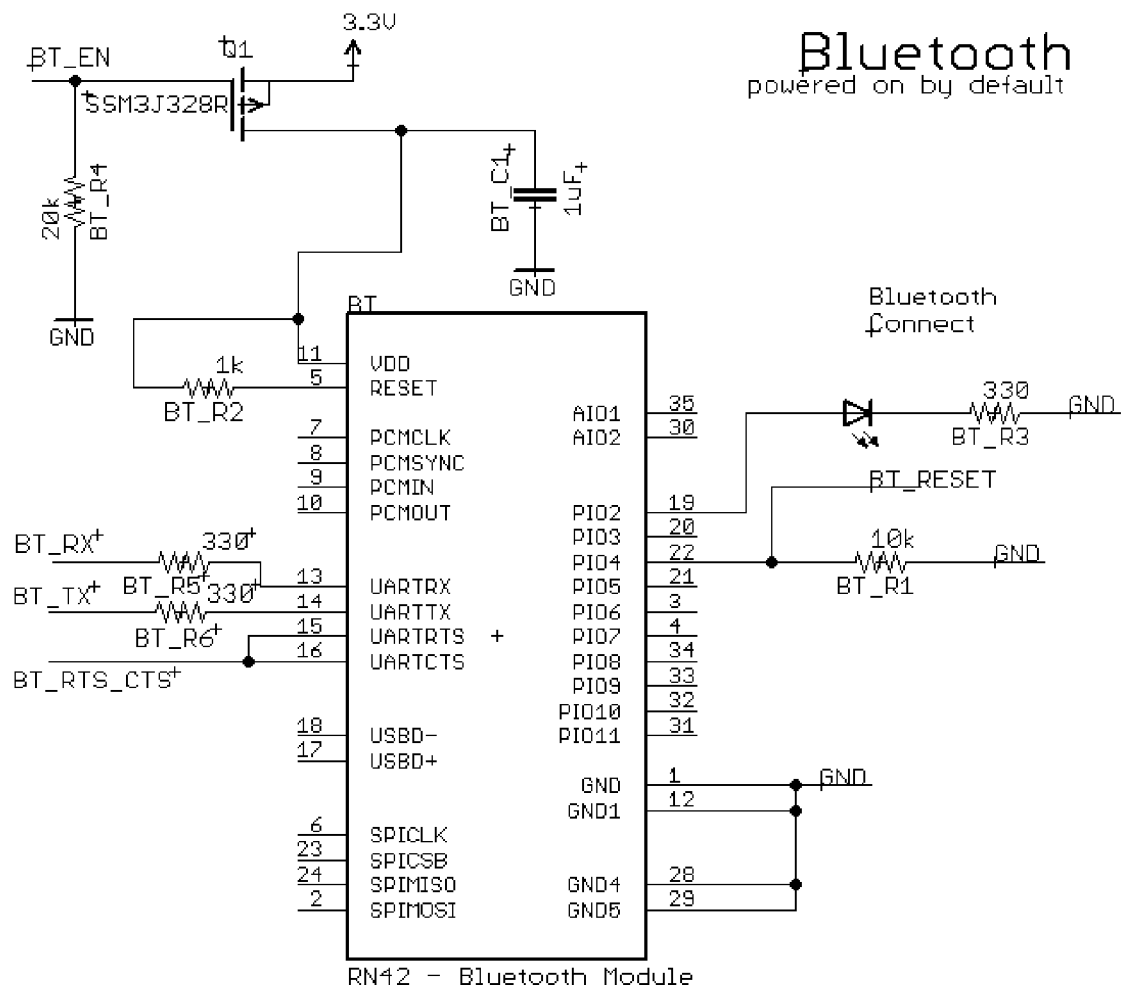
Figure 4G:
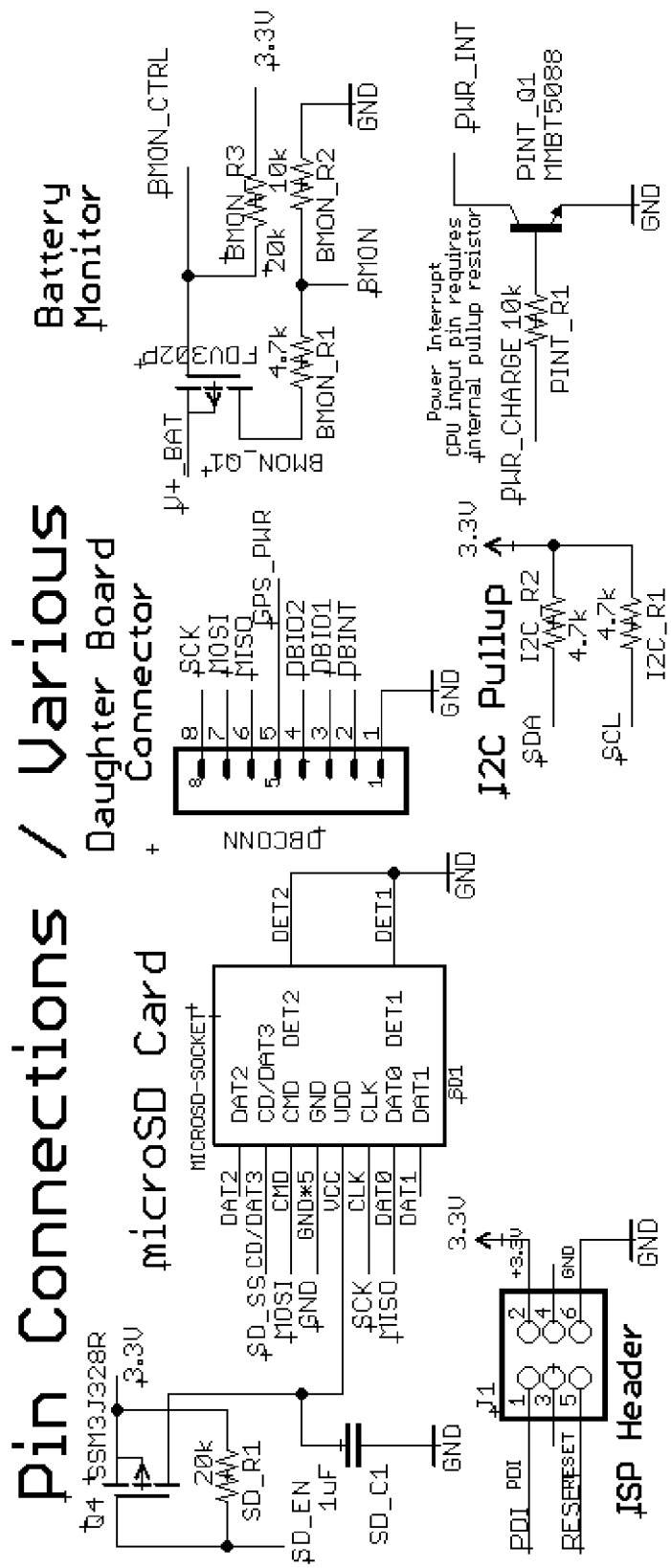
Figure 4H:
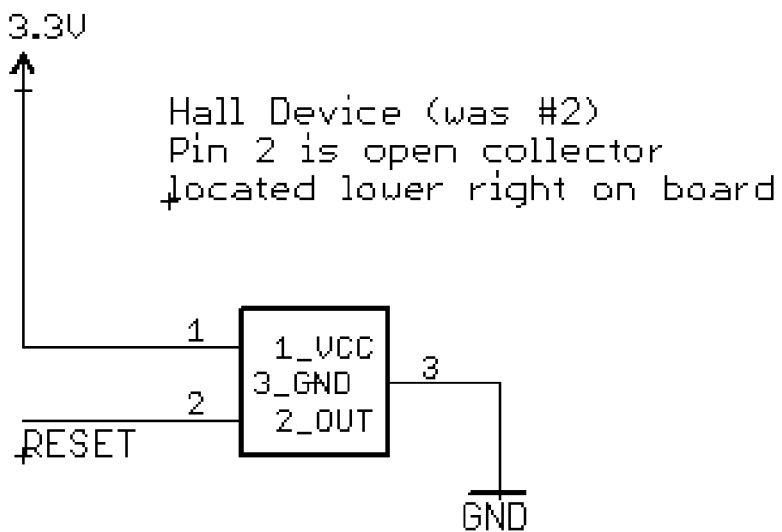
Figure 4I:
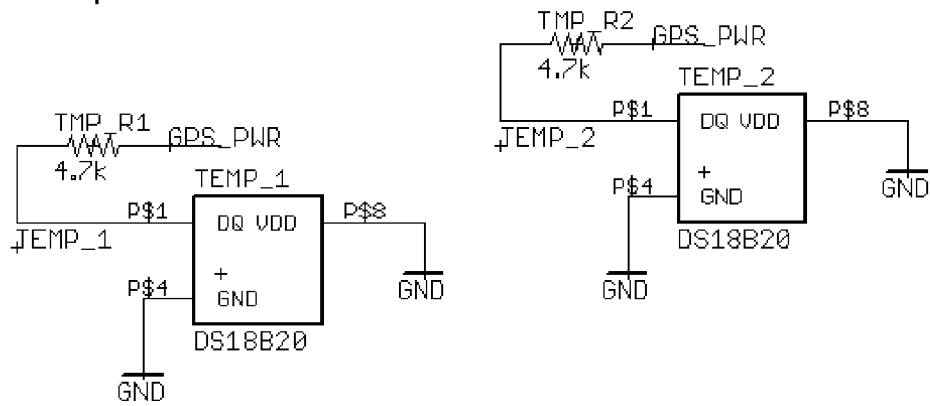
Figure 4J:
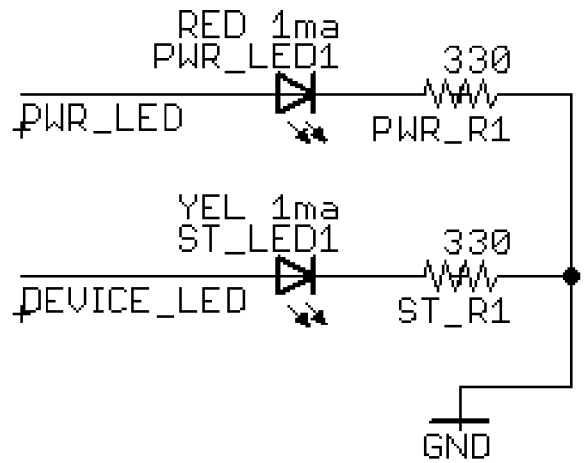
Figure 4K:
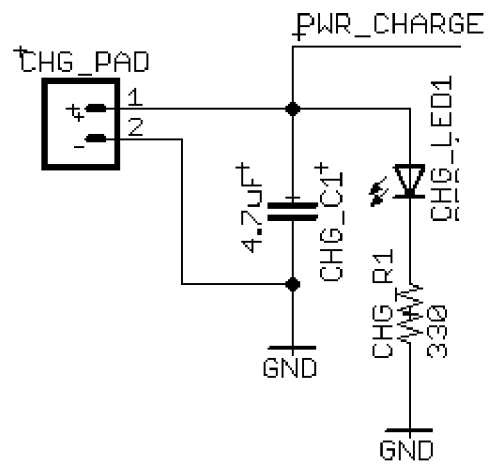

FIGS. 4(A)-4(K) show aspects of sensing device circuitry in accord with at least some aspects of the present concepts. FIG. 4(D) applies when the Qi receiver is included as discrete components. FIG. 4(K) applies when the Qi receiver is a separate module.

FIGS. 5(A)-5(D) are listings of components of the sensing device circuitry in FIGS. 4(A)-4(K). FIGS. 5(A) and 5(B) apply when the Qi receiver is a separate module. FIGS. 5(C) and 5(D) apply when the Qi receiver is included as discrete components.

By way of example, a "Storage" or inactive state can be entered whenever there is a lack of sufficient motion for a specified period of time, 5 minutes by default, and there is no detection of being "in the water" by a salinity detector or by other means. In this state, all of the measuring devices will either be in a low power state or de-energized, and the CPU will operate in 'power down standby' mode as shown in Table 1, below, which presents for illustration one non-limiting embodiment of the present concepts.

TABLE 1

| On-board Device | Storage State |
|---|---|
| CPU | Power-down standby |
| IMU | Low power accelerometer-only with periodic wakeup |
| Temperature Sensors | OFF |
| Salinity/Conductivity Detector | OFF |
| pH Detector | OFF |
| GPS | OFF |
| Bluetooth | OFF |
| Qi Charge Receiver | inactive |

In accord with at least some aspects of the present concepts, the Inertial Measurement Unit ("IMU") uses a built-in periodic "wakeup" mode to check for acceleration, which in at least one case is configured to only check the X and Y directions for motion to limit power consumption in this state. The gyros and magnetic circuits are also powered down. If the IMU detects acceleration above a preset threshold, it will issue an interrupt to the CPU. On interrupt, the CPU will then restart itself and check for the current conditions. If the interrupt was due to motion from the IMU, and a charger is not currently connected with the Qi receiver, it will enter the "Recording" state. The device will monitor and record all measured parameters until there is no sufficient motion for a pre-determined time, which is by default 5 minutes, at which point it will close and truncate any open log file, and re-enter the "Storage" state. As noted above, in accord with other aspects of the present concepts, a user may be enabled to selectively activate the IMU and/or other system components manually via a user-input device, such as, but not limited to, one or more buttons, a touch pad, or a connected electronic device (e.g., a smart phone connected to the device via a wireless connection).

If the CPU interrupt was caused by a "charging" detect (Qi charger active), the Smartphin will immediately enter the "Charging" state.

Periodically the CPU is capable of "waking up" to check the battery voltage. It also checks battery voltage while in the "Recording" state. If at any time (other than in the "Charging" state) the battery voltage is detected as being below the "low voltage" threshold, the CPU will de-energize ALL on-board devices (including the IMU) and place itself into a "Power-Down Standby" state to minimize additional current draw from the battery. This is similar to the "Storage" state except that it will not be awakened by motion detection. During the "Recording" state, measured battery voltage is recorded along with the other data.

The charging state, represented by way of example, for one embodiment, in Table 2 below, is initiated whenever the Qi charger is activated, regardless of the current battery state. If the batteries have been completely drained, this will also cause a re-boot of the CPU as it powers up. To prevent rapid reboot or other undesirable conditions, the regulator circuit has been designed to prevent the CPU from energizing whenever battery voltage drops below a "low voltage threshold". When leaving the "Recording" state, the open data log file is first closed, then truncated, to ensure data reliability. The GPS, environmental measurement, and temperature devices are de-energized. When entering the "Charging" state, the Bluetooth device is energized and set to "factory default", then immediately re-configured to run at a significantly higher baud rate.

TABLE 2

| On-board Device | Charging State |
|---|---|
| CPU | active |
| IMU | OFF |
| Temperature Sensors | OFF |
| Salinity/Conductivity Detector | OFF |
| pH Detector | OFF |
| GPS | OFF |
| Bluetooth | ON |
| Qi Charge Receiver | Initially Active; inactive for 5 minutes to end Charging State. |

Communications with the Bluetooth device may be initiated once the red "power" LED begins to blink at a ½ Hz rate. Communications may be re-initiated at any time, so long as the Qi charger remains active, or the time without communication is less than 5 minutes.

When there has been a lack of Qi charger activation and Bluetooth activity for 5 minutes, the device will reset itself and go into the "Storage" state.

In accord with the present example, a CPU reset, which by example may be initiated using a physical, magnetic, or other type of switch, will simply re-initialize all of the various components and enter the "Recording" state. However, if the Qi charger is active, the boot loader will perform a factory reset on the bluetooth device and enable "Flash Mode". Once the boot loader has enabled "Flash Mode" 60 seconds are provided for a communication device to connect to the Bluetooth and initiate a firmware update. "Flash Mode" is indicated by a series of LED blinks, first with the "Power" LED on solid, and then off, for a time period of around 6 seconds. When the Power LED is off AND you get 3 rapid blinks on the device LED, the Bluetooth device is ready to accept a connection. At this point the 60 second delay starts. If the firmware update program does not instruct the boot loader to begin updating the firmware at the end of the 60 second delay, a normal reboot will occur, and the device will enter Charging mode or Transport mode, depending on the state of the Qi Charge Receiver.

The "Recording" state, represented by way of example, for one embodiment, in Table 3 below, is initiated following the "Storage" state by detected motion via the IMU. There are two operating modes in the "Recording" state, consisting of 'minimal' and 'high speed' data recording modes. Whenever detected motion remains below a second 'low speed recording' threshold for a period of time, which by default is 15 seconds, only a minimal amount of data is recorded. The default time period for IMU data during the 'minimal' mode is 5 times per second. IMU data continues to be measured at the normal rate (which by default is about 90 times per second), but not recorded. Other data, such as battery voltage, GPS coordinates, temperature, salinity, or pH, are still recorded at their normal rate.

TABLE 3

| On-board Device | Recording State (minimal mode) |
|---|---|
| CPU | Active |
| IMU | 5 times per second (by default) |
| Temperature Sensors | ON |
| Salinity/Conductivity Detector | ON |
| pH Detector | ON |
| GPS | ON |
| Bluetooth | OFF |
| Qi Charge Receiver | inactive |

The device is also capable of entering a "Periodic" recording mode, which is independent of motion, in which environmental data is recorded at periodic intervals. In this state, IMU data recording is optional, and the device 'wakes up' at specified time intervals, and records for specified periods of time, then goes back into a 'Power-Down Standby' state until the next recording period causes it to 'wake up' and record data again. This mode facilitates capturing data over longer periods, for example if the Smartphin was deployed on a boat crossing the Pacific Ocean. The Periodic recording would enable the battery life to be extended. In at least some aspects of the present concepts, the interval is programmable or user-selectable and may further optionally comprise a plurality of selected intervals with each interval being triggered by an event such as a time-based event or a location-based event (e.g., position).

If a salinity detector is utilized in combination with the other aspects of the present concepts, it has the capability of measuring a value that indicates that the device is "in the water". So long as readings from a salinity or other kind of detector determines that the device is "in the water", and not charging, it will not leave the "Recording" state. This helps to prevent the need to re-start the system, should motion while in the water fall low enough to cause the device to enter the "Storage" state, since a short period of time is needed to reset all of the connected devices and begin recording again, and thereby cause important motion data to be missed.

When there is a lack of sufficient acceleration for more than a pre-determined time, which is by default 5 minutes but could be set to any other desired pre-determined time, the Smartphin will go into the "Storage" state. This is to save as much battery life as possible whenever the Smartphin is "at rest". Additionally, the Smartphin will check its battery voltage to see if it is below the "low voltage" threshold. If the battery voltage is detected as being below the "low voltage" threshold, the CPU will first stop all data recording (closing the file and truncating it to the current record), de-energize ALL on-board devices (including the IMU) and place itself into a "Power-Down Standby" state to minimize additional current draw from the battery. This is similar to the "Storage" state except that it will not be awakened by motion detection.

When the Smartphin has detected sufficient motion above a threshold that is adjustable (e.g., a delta or differential of IMU data from one measurement to the next corresponding to a predetermine change in acceleration, velocity, orientation, etc.), represented by way of example, for one embodiment, in Table 4 below, it switches to the "Recording" state 'normal' mode, recording with high sample rate IMU data, as well as environmental data and GPS location data. Below the 'low speed recording' threshold, only a fraction of the IMU data is recorded. But whenever motion exceeds the 'low speed recording' threshold, all of the IMU data is recorded, at a default rate of about 90 times per second. Subsequently, if motion remains below the 'low speed recording' threshold for a period of time that is by default 15 seconds, the device will re-enter 'low speed' mode and record data accordingly.

TABLE 4

| On-board Device | Recording State (normal mode) |
| --- | --- |
| CPU | Active |
| IMU | 90 times per sec (by default) |
| Temperature Sensors | ON |
| Salinity/Conductivity Detector | ON |
| pH Detector | ON |
| GPS | ON |
| Bluetooth | OFF |
| Qi Charge Receiver | inactive |

When a sufficient salinity level is present, the salinity detector is capable of re-charging its capacitor through the salinity probes themselves. This enables faster charging, and more frequent measurements of salinity. Additionally, reversing the polarity of the probes may decrease ionic migration and therefore salt deposition on a probe. Experimentation has shown that frequent salinity measurements are actually more accurate and, more likely, to stabilize within a short period of time following the immersion of the salinity probes. Typically it may take up to 5 minutes for the readings to stabilize. Dry probes may have accumulated material on them, and 5 minutes worth of salinity measurements while immersed in water seems to be sufficient to "clean them off" enough to get good readings. As to the sufficiency of the salinity level in a particular embodiment, the salinity threshold is derived from an inverse conductivity measured value and when this measured value exceeds a threshold, the conductivity is deemed too low for a normal "ocean water" salinity value (e.g., about 3.5% or 35 g/L), and a "not in the water" state is assigned. The threshold value is adjustable.

Whenever a salinity detector is included in the device, salinity records will be captured at a lower rate if the salinity value shows that the device is not 'in the water', which is by default every 30 seconds. Once the salinity indicates that it is, in fact, 'in the water', the salinity capture is more frequent, by default every 2 seconds. A typical 4 conductor salinity probe is tolerant of drying out, but requires a short period of time to stabilize when first entering the water. This must be considered when analyzing the data.

Additionally, when a surfer is heading out to where the waves are, he or she is typically going to remain in-place for a significant amount of time, waiting for a decent wave. The amount of time paddling the board out to a good location, plus the waiting time for a wave, is likely to be long enough to capture at least one good salinity reading. Once the surfboard is on a wave, however, the Smartphin may actually ride out of the water for short periods of time. The salinity detector and device firmware can indicate when the Smartphin is in the water, and when it is not, and coordinate this with temperature readings and additional salinity readings. For this reason, there is a 5 minute timeout on the salinity readings NOT indicating "in the water" before the Smartphin will change to the "Transport" state.

As with the "Transport" state, the Smartphin will monitor battery voltage. If the battery voltage is detected as being below the "low voltage" threshold, the CPU will first stop all data recording (closing the file and truncating it to the current record), de-energize ALL on-board devices (including the IMU) and place itself into a "Power-Down Standby" state to minimize additional current draw from the battery. Again, this is similar to the "Storage" state except that it will not be awakened by motion detection.

A typical surf session will put the Smartphin through all of its states, in a predictable manner. Beginning with the "Storage" state, the surfboard (with the Smartphin attached) will enter the "Recording" state as soon as it is moved, most likely when being loaded onto a vehicle. If present, the salinity detector will detect that it is not submerged in sea water, but data will still be recorded.

While being transported, the charger can be placed over the Smartphin in order to make sure the battery is properly charged during the trip, placing it into the "Charging" state, and stopping all data recording. This may also happen beforehand, with a final short-duration charge done from within the vehicle during transport, or just prior to moving the board to the water. In any case, the Smartphin will enter the "Charging" state, and enable bluetooth communication. If the user chooses, he or she may transfer whatever data is on the Smartphin at that time to the online repository, or store it on his or her smart phone or other bluetooth capable computing device for later transfer.

After arriving at the beach, the surfboard (with Smartphin attached) is removed from the vehicle and transported to the ocean. IMU data will be logged, as well as temperature and other environmental data, and GPS information. Even though initial recordings of environmental data may not be valid, these results will be post-processed by scientist once the data is moved to a public server.

While surfing, the Smartphin occasionally leaves the water. If a salinity detector is present, the Smartphin requires that salinity indicate "out of the water" for the 'no motion' time period, by default 5 minutes, before it will allow transition back into the "Storage" state.

On several occasions a surfer may rest on the beach for a while, leaving his or her board out of the water. During these times, the Smartphin will transition from the "Recording" state to the "Storage" state. And if the user wants to, he or she may choose to transfer data right away by using a charger in his or her vehicle and performing a data transfer with his or her smart phone, while the Smartphin is in the "Charging" state.

At some point the surf session is over, and the user may transfer his or her surfboard (with the Smartphin attached) back to his or her vehicle. Ideally he or she will place the charger on the Smartphin and perform a data transfer while the Smartphin is in the "Charging" state. Alternately this may be done once the surfer returns back home.

Finally the surfboard is stowed away, and the Smartphin transitions to the "Storage" state, using minimal current to detect if there is any motion.

In case the battery might drain to a point where voltage is too low, the Smartphin will occasionally wake up and test for this condition. If the battery voltage is too low, it will power off the IMU and go back into "Power-Down Standby", with an absolute minimal current draw. In this state motion will not wake up the Smartphin. It will be necessary to charge the battery first.

In at least some aspects, the sensor device 100 optionally comprises at least one switch comprising a manually actuatable switch. The manually actuatable switch could comprise a conventional push-button switch utilizing a short-stroke displaceable actuator (e.g., responsive to pressure) or, alternatively, could comprise a small touch screen button (e.g., responsive to a capacitive input, a resistive input, etc. from a user's finger). The sensor device 100, or the manually actuatable switch, may optionally comprise one or more LED lights (e.g., a green LED) to provide a visual indicate of one or more variables (e.g., on/off, battery charge, transmitter operability, etc.).

In at least some other aspects, the water-sports board switch is automatically actuated from the first state (e.g., off) to the second state (e.g., on) responsive to immersion in water, and vice versa upon removal from water, based on a sensed characteristic and/or completion of an external circuit by the water. For example, a switch is operatively associated with a conductivity sensor, and the switch is automatically actuated from the first state to the second state responsive to a conductivity change (i.e., immersion in salt water, which is a very efficient electrical conductor), greater than a predetermined threshold, sensed by the at least one sensor. For example, seawater has a resistivity ($\rho$) of $2\times10^{-1}$ $\Omega \cdot m$ at 20° C. and a conductivity ($\sigma$) of 4.8 S/m at 20° C., whereas air has a resistivity ($\rho$) of $1.3\times10^{16}$ to $3.3\times10^{16}$ $\Omega \cdot m$ at 20° C. and a conductivity ($\sigma$) of $3\times10^{-15}$ to $8\times10^{-15}$ S/m at 20° C. These differences can be used by the sensor device 100 to differentiate as to whether the device is in the air (and should advantageously be in a quiescent state) or in the ocean, where it should activate to obtain environmental data (and optionally water-sports movement data).

In other aspects, the sensor device 100 optionally comprises a salinity sensor and the salinity sensor is used to automatically actuate a switch to change a state of the sensor device from a first state (e.g., off, asleep, low-power operation, etc.) to a second state (e.g., on) responsive to change in salinity, greater than a predetermined threshold (e.g., from substantially zero to between about 3.1-3.9%), sensed by the at least one sensor. Likewise, upon removal from the water, the sensed salinity decreases from a steady state between about 3.1-3.9% back to a lower value, thus causing the switch to actuate to change a state of the sensor device from the second state back to the first state responsive to the change in (e.g., decrease in) sensed salinity.

The sensing device(s) 100 sensor(s) may comprise, for example, one or more temperature sensors, one or more water salinity sensors, one or more conductivity sensors, one or more pH sensors, or a combination thereof.

Figure 2A:
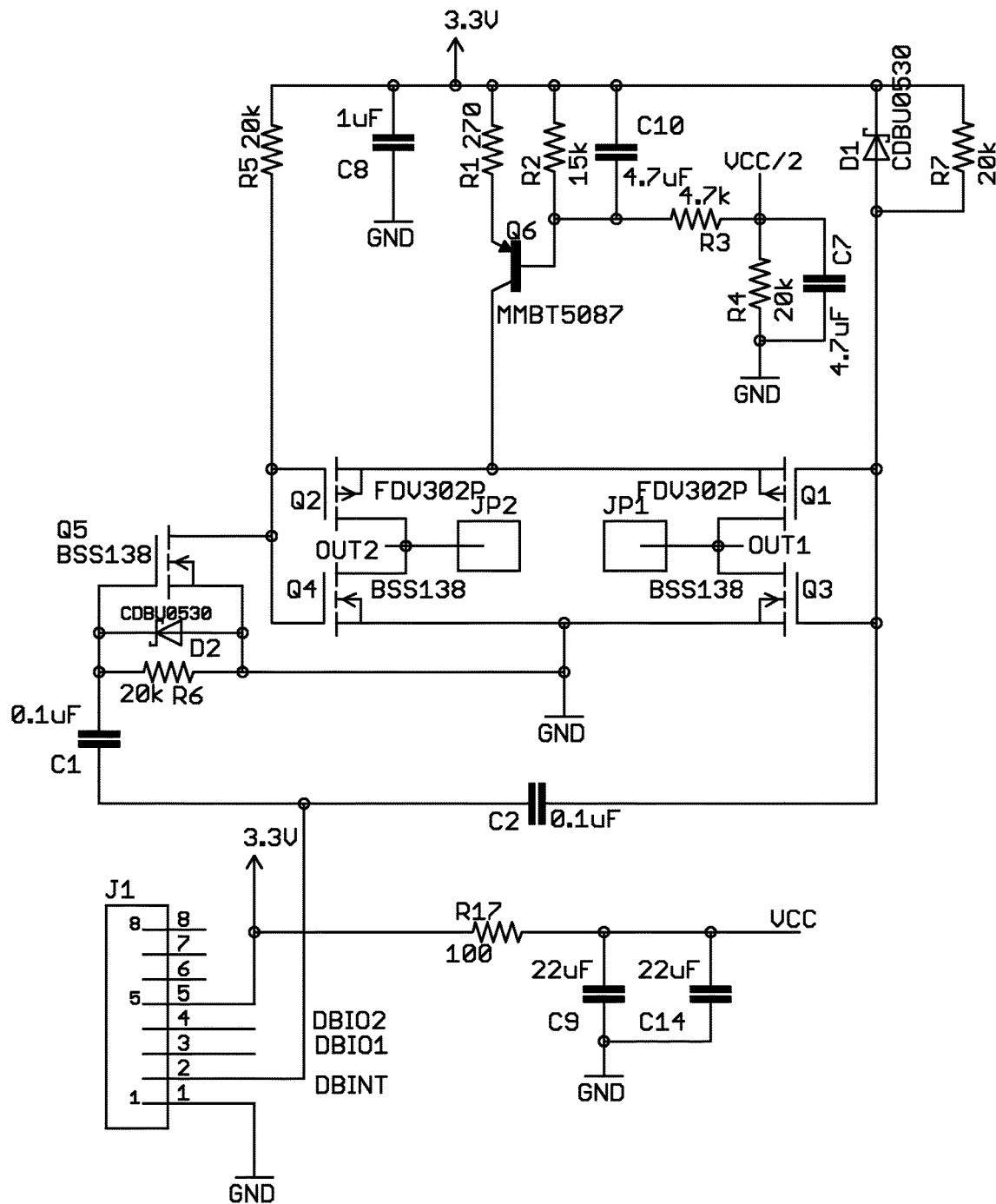
FIG. 2 is a schematic representation of a 4-conductor salinity circuit for collecting environmental salinity data according to at least some aspects of the present concepts.
Figure 2B:
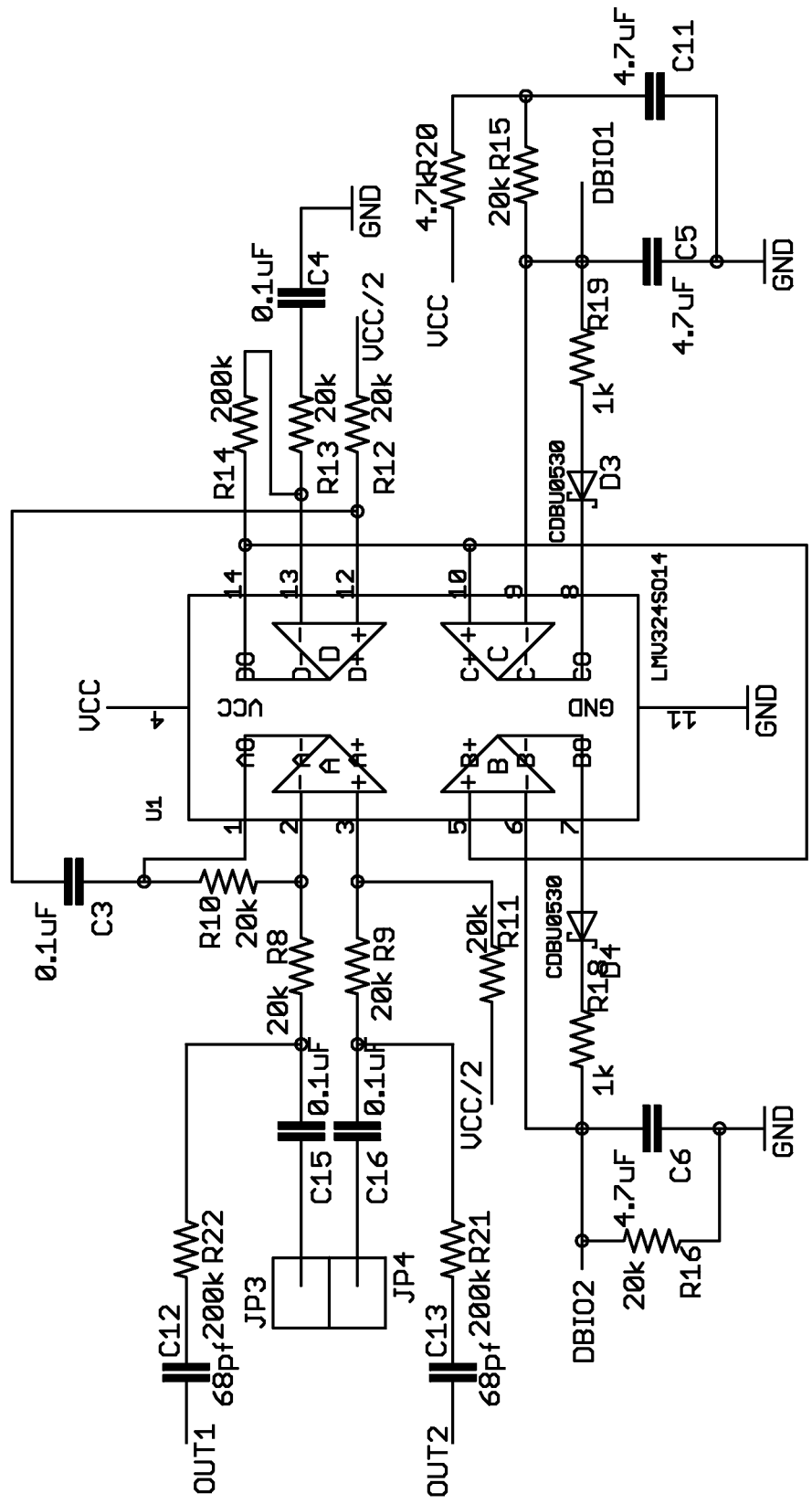

One aspect of a salinity measurement sensor circuit in accord with the present concepts is shown in FIG. 2. The depicted salinity measurement circuit is configured to measure conductivity using a 4 conductor conductivity probe, in which an AC signal is coupled from one set of probes to another according to the amplitude of the coupled signal being roughly proportional to the inverse of the water conductivity.

The salinity of seawater, for practical purposes, is considered directly proportional to its conductivity, when the water temperature, probe surface area, and the distance between them is constant. However, because of the many variables in the relationship between conductivity and salinity, it is necessary to calibrate the salinity measurement against known concentrations of salt in water, and also compensate for temperature. Additionally, the salinity probes must consist of a material that is not very susceptible to corrosion or oxidation/reduction reactions when placed in salt water and with an electric current applied.

To minimize the effect of electroplating and salt deposition, the salinity circuit uses an AC signal and DC blocking capacitors, as well as a non-reactive probe material such as graphite or blackened platinum.

As shown in the example of FIG. 2, the salinity sensor circuit comprises a constant current (Q6, R1) 'H' bridge (Q1 through Q4) to drive the AC signal through one set of probes, and a differential AC amplifier (U1$a,d$) and pair of 'peak' detectors (U1$b,c$) to measure the induced signal on the other set of probes, for a 4 conductor conductivity probe. By using a constant current AC signal, the actual induced voltage should be more linearly representative of the effective resistance (i.e. inverse conductivity) of the water, thus improving accuracy. The two 'peak' values are then measured via a differential A/D converter, and their voltage difference becomes the measured signal.

FIG. 2 also shows that a small 'bypass' signal is coupled via C12, C13, R21, and R22 from the H bridge to the differential amplifier in order to ensure that a large signal appears when the probe is dry or removed from the water. Higher conductivity results in a lower measured value, and low conductivity in a high measured value. As such, when not in the water, the conductivity should be zero, resulting in a very large measured value. However, in actual practice, a dry probe has an indeterminate signal, which does not suit the ability to accurately measure salinity and 'out of the water' conditions, and may be high, low, or anywhere in between. Therefore, to correct for this, the bypass signal is applied through a high impedance series circuit. A dry probe exhibits a high impedance state across the measurement electrodes, allowing a comparably high impedance RC circuit to be used to essentially 'leak' a signal as if the probe were in water with very low conductivity. But whenever the conductivity probe is in salt water, the effect of these capacitors and resistors is negligible, thereby providing a reliable 'in the water' indication without impacting the conductivity measurement.

Whenever the processor(s) make(s) a salinity measurement, it first puts an AC signal of at least 8 khz on pin 2 of the daughter board connector (labeled 'DBINT') to energize the H bridge. This couples the AC frequency through the water to the differential AC amplifier U1a and U1d. DC blocking capacitors C15 and C16 ensure that no induced DC will pass through, improving accuracy and preventing certain kinds of drift.

The peak detectors U1b and U1c operate as 'ideal diodes' in a sample and hold configuration, essentially measuring the high and low peak of the resulting AC waveform from the differential amplifier. The capacitors C5 and C6 maintain their charge for a sufficiently long enough period of time as to remain accurate and eliminate a large quantity of noise. This value is measured by the CPU's differential A/D converter from pins 3 and 4 on the daughter board connector (labeled 'DBIO1' and 'DBIO2').

The CPU allows the AC signal to stabilize for 1 second, then averages as many readings as it can for an additional 1 second, to minimize the effects of noise and improve overall accuracy. Once the measurement is complete, the AC signal on pin 2 (labeled 'DBINT') is stopped. This effectively turns the salinity circuit off, though power is still supplied on the 'GPS' power circuit.

When there is no salt water exposed to the probes, a 'maximum' value results due to the high impedance 'bypass' circuit, indicating that the device is 'out of the water'. A threshold for 'out of the water' can be configured, and is by default 50% of the maximum possible reading. Values above this threshold are considered to be 'out of the water' and invalid.

When the device is immersed in salt water, the signal level is well below the 'out of the water' threshold for the normal range of ocean water salinity. The selection of R1, which determines the H bridge current level, is such that the normal range of values from ocean water will fall well below the 'out of the water' threshold, and at a value high enough to ensure proper precision and accuracy. A typical raw value might be in the neighborhood of '700' for normal ocean water at 65 degrees Fahrenheit.

Conductivity through a salt solution is directly proportional to the surface area of the salinity probes, and inversely proportional to the distance between them. Even when an AC current is rapidly pulsed through the salt solution (as it is being done here), some non-linearity can be introduced simply because of the behavior of various ions in the solution. Additionally, since seawater has more than just sodium and chloride ions, these other ions can interfere with the measurements to some extent. So some inaccuracy is inherent in the measurement itself, which can only be accurately performed using chemical means (such as a titration or precipitation measurement). However, when the range of concentration is relatively small, and the non-linearities are properly compensated for, the measurement accuracy can be retained. Further, the 4-conductor probe design with AC signal coupling is well known to be one of the most accurate non-chemical means of determining conductivity and salinity.

Figure 3A:
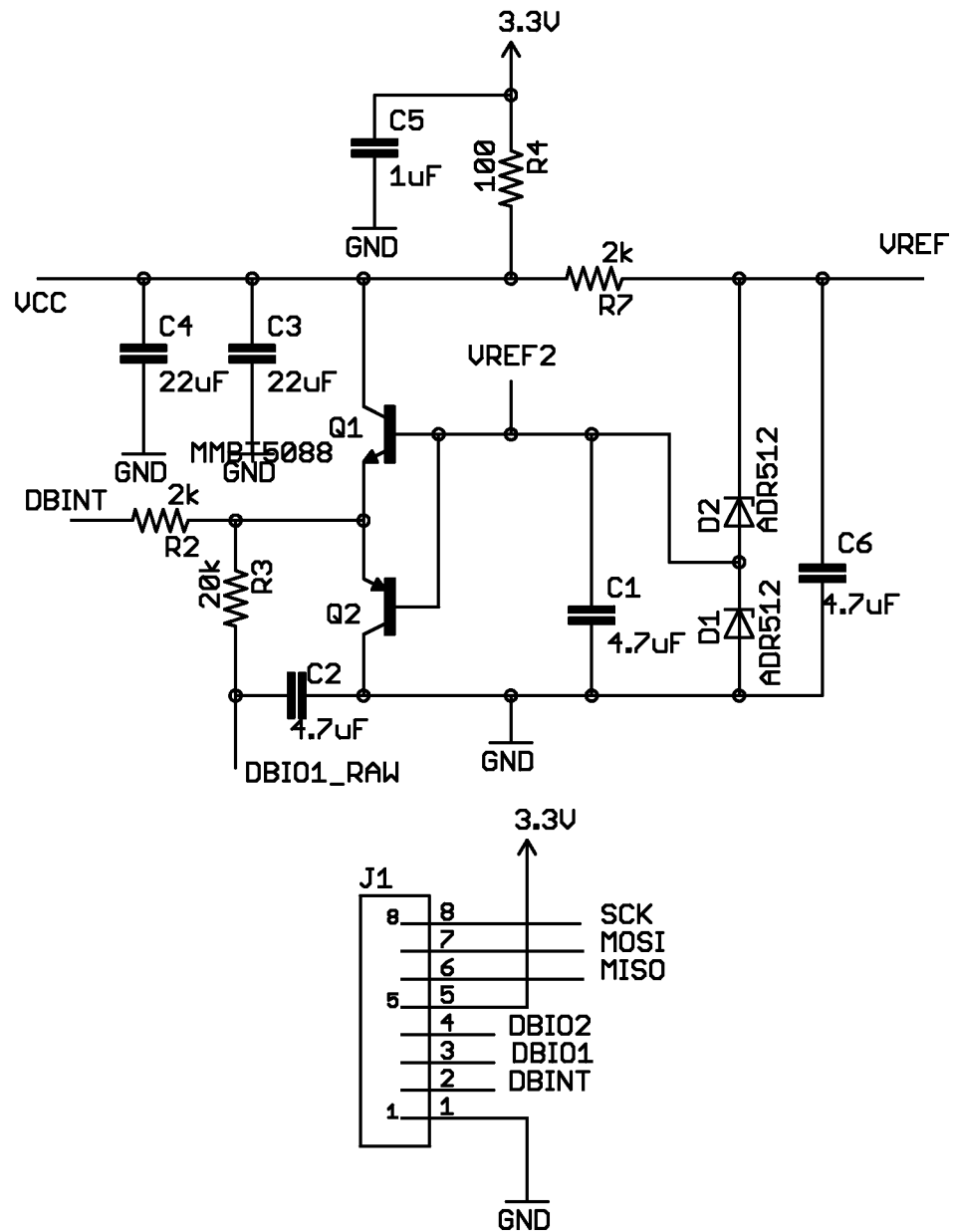
FIG. 3 is a schematic representation of a pH measurement circuit using a connected ion sensitive field-effect transistor (ISFET) used for measuring ion concentrations in solution and reference electrode according to at least some aspects of the present concepts.
Figure 3B:
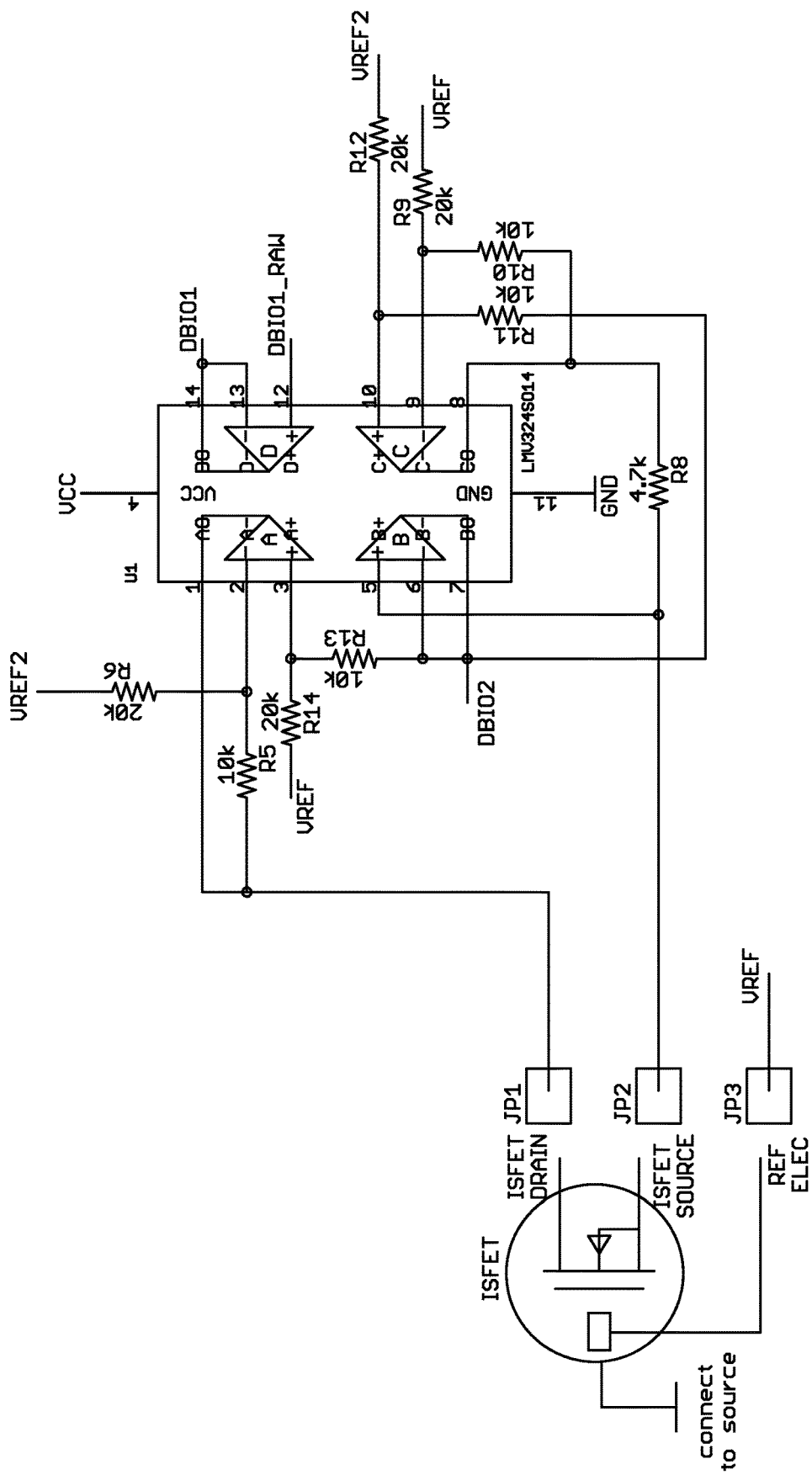

In the pH circuit of FIG. 3, an ISFET is used as the detector, with a standard KCl+Ag reference electrode. The voltage difference between the Gate of the ISFET (which is behind an ionic barrier), and the reference electrode, is generally proportional to the pH of the measured solution, very similar to a glass bulb probe. The operational amplifier U1 regulates the voltage across the Drain and Source of the ISFET, as well as the amount of current flowing through it, maintaining both of them constant, such that the voltage on the Drain accurately tracks the Gate voltage, and therefore the pH.

In FIGS. 3, Q1 and Q2 clamp a PWM signal supplied by the CPU on 'DBINT', which is pin 2 of the daughter board connector. This signal adjusts a reference voltage, which is further filtered and buffered as 'DBIO1' on pin 3 of the daughter board connector. During initial calibration, a 'zero' is performed in which the PWM signal is adjusted to generate a 'zero' result for a specific pH solution, usually a value below 7.0. This calibration is not critical, but doing it properly improves precision. Measurements on the ISFET Source are buffered via U1b and applied to 'DBIO2' on pin 4 of the daughter board connector. The CPU will then compare DBIO1 to DBIO2, and the resulting differential A/D comparison will become the raw value for pH.

The calibration process determines how to map the raw pH values as measured from the circuit in FIG. 3. Measurements of known pH and temperature are made, and an appropriate calibration curve is generated on the server that translates the raw pH and temperature values into accurate pH values. Therefore, raw data values are always captured for pH data, and then calibration is applied by the server before displaying the data.

To improve A/D accuracy, a method is applied by the firmware on the A/D value to change its amplification factor as needed, so that very small values can be measured accurately, while still retaining the ability to measure large values. In one example, the gain can be adjusted from a value of ½ to a value of 64, based on the CPU's capabilities. This extends the 12-bit A/D's capabilities significantly, being able to measure the very small voltages that you would typically have for a pH measurement.

To improve accuracy, the processor will average pH data sensed over a predetermined period of time (e.g., 0.5 seconds, 1 second, 2 seconds, etc.) before recording the result. This helps to eliminate the effect of external noise on a very high impedence circuit. Noise sources exist on the circuit board itself, as well as external to the device. Assuming that the noise exists and then eliminating its effect helps to ensure proper accuracy.

Although the present concepts may advantageously utilize a variety of conventional materials for the salinity probe(s), the presently preferred materials for the salinity probe(s) comprise 'blackened' (aka 'platinized') Platinum or Graphite, which have the least potential for chemical reaction in a galvanic cell. Graphite works well with a 4-conductor AC probe, and is the lower cost solution. Many commercial 4-conductor cells use graphite conductors, often in a concentric configuration, where the outer 2 probes couple the AC signal to the inner 2 probes. The appearance is similar to a 'bullseye' on a target, with the outer graphite probe encircling the inner graphite probe on each of two opposing surfaces, and with the ocean water flowing in between the 2 sets of probes. This concentric configuration appears to work best for conductivity measurements, with the graphite probes.

In each of the above examples of a switch or switches being used to cause a change in state of the sensor device 100, the sensor device may further comprise a timer configured to automatically change the sensor device from the second state to the first state, or from the first state to the second state, following satisfaction of a respective triggering condition (e.g., motion, change in resistivity, change in conductivity, change in salinity, etc.) or input (e.g., depression of a manually actuated button, magnetic field applied to a hall sensor, etc.), and further following a lapse in a predetermined period of time. Thus, a delay of 5 seconds, 15 seconds, 30 seconds, 1 minute, 2 minutes, 3 minutes, 4 minutes, 5 minutes, or longer periods, or periods intermediate thereto, could be used to ensure that a temporary condition (e.g., a surfboard going airborne or flipping over) doesn't deactivate the device to thereby require reactivation. During such period, the environmental data sensed by the sensor(s) of the sensor device 100 may advantageously be flagged, omitted from storage, or otherwise characterized as suspect.

To facilitate utilization of the sensor device(s) 100 in a water-sports board (or other water-sports gear, attire, or equipment) to collect environmental data, the sensor device(s) 100 may advantageously comprise at least one water-sports sensor configured to sense movement-based data relating to the water-sports activity. For example, in at least some aspects of the present concepts, the sensor device(s) 100 comprises one or more of a three-axis accelerometer, a three-axis magnetometer, a three-axis gyroscope, or combinations thereof, such water-sports sensor(s) being configured to determine an orientation of the water-sports sensor(s) relative to one another or relative to a mounted position and/or motion of and/or orientation of the water-sports sensor(s) relative to one another or relative to one or more reference points.

To facilitate the integrity of data collection, the sensor device(s) 100 may comprises a GPS unit configured to enable determination of a location of the sensor(s) devices, wherein the processor(s) of the sensor device(s) are configured, while the at least one switch is in the second state (e.g., on), to determine whether a location of the sensor device(s) corresponds to a nearshore environment and to cause storage of data sensed by the sensor(s) in the memory device only when the location corresponds to a nearshore environment. Such determination could be performed either within the device itself, or in the post-processing of transferred data by the servers. Thus, if a paddle board or a windsurfing board utilizing the sensor device(s) 100 is used both in an inland water body (e.g., a lake) and in a nearshore environment, the collection or display of data from the sensor device(s) would be enabled when the device or servers can verify, using the GPS unit, that the sensor device(s) are disposed in a nearshore environment where such data collection is appropriate. Moreover, such location-based differentiation enables the servers 160 that aggregate data from a plurality of such sensor device(s) 100 (e.g., thousands, tens of thousands, hundreds of thousands) over a plurality of uses of each of such sensor device(s), to parse the environmental data by characteristics such as, but not limited to, distance from the shoreline, latitude, longitude, disposition relative to known man-made or geological features, depth (where the sensor device(s) comprise a depth gauge, etc.) to appropriately characterize the received data.

The sensing device(s) 100 optionally, but advantageously, comprises a transmitter 120 disposed within the sensor housing By way of example, one suitable transmitter is the RN42-I/RM Bluetooth/802.15.1 Modules Class 2.1 Bluetooth module w/ antenna, manufactured by Roving Networks of Microchip Technology Inc., Chandler, Ariz., US. The transmitter 120 is configured to transmit sensor data (represented as 130 in FIG. 1) to an external device 140, disposed either locally (e.g., a user's smart phone, a device connected to the transmitter by a personal area network, etc.) or remotely (e.g., directly to a computer or server 160 disposed in a location far from the transmitter as represented by reference numeral 132 in FIG. 1, etc.), in real-time (e.g., on the fly, directly to a user's borne personal electronic device or to a remote device, etc.) and/or at a later time (e.g., post water-sport activity, transmitting sensor data stored in the memory device), depending on selection of transmitter functionality for the sensing device(s).

In the embodiment depicted in FIG. 1, the transmitter 120 is configured to transmit the sensor data to an external local device, a smart phone 130 as shown, via a Bluetooth connection. Alternatively, the transmitter 120 is configured to transmit the sensor data to an external local device 130, via one or more other types of local wireless (or hardwired) via another communication protocol, such as, but not limited to, spread spectrum frequency-hopping, wife, xbee, ZigBee, ISA100.11a, WirelessHART, MiWi, or IEEE 802. Of course, in other aspects, the sensor device(s) 100 may simply transmit the sensor data to an external local device 130 (e.g., smart phone, laptop, desk top computer, tablet computer, etc.) via a cord or cable appropriate to a convention I/O port on each of the sensor device 100, or common to a plurality of sensor devices 100, and a respective external local device 130.

Desirably, the sensing device(s) 100 may implement, in lieu of or in additional to sensor-based modalities that control activation of the sensing device(s) based on sensed physical characteristics of the immediate environment (e.g., salinity, pH, etc.), the processor(s) may be configured to execute instructions stored on the memory devices that cause the processor(s) to determine a status of use by the motion of the sensing device(s) characteristic to such use.

FIG. 1 is a schematic representing at least some manners of communication and transfer of data from the sensing device(s) 100 transmitter 120 either directly to a remote device (e.g., servers 160) or to an intermediate external device 140 and then to the remote device. The present concepts also include an "Application," hosted by a web server, configured to communicate with user's transmitter 120 or external device 140 (e.g., smart phone, laptop, tablet, watch, other computing device, etc.) and receive the data transmitted from such device, performing conventional acts such as authenticating the user and ensuring that the data sets are complete, not broken. The application is programmed using any high-level database and/or website application language capable of providing conventional web app service functionality such as, but not limited to, Django, Rails, PHP, and SQL.

The application is then configured to generate a human-readable file for each data transmission (e.g., a surf session) by converting the uploaded data from a binary format to human-readable format, which is then loaded into a single file to facilitate manipulation by the user. Such file is also advantageously aggregated for the user in a database or library of the user's past data uploads.

Although the collection of viable or useful environmental data is a primary focus of the present concepts, the present concepts also recognize the desirability for collection of motion-based data and presentation of such motion-based data in a format that provides the user with sports-based performance feedback. By way of example, the sensing device(s) 100 accelerometers, magnetometers, and/or gyroscopes, can graphically represent a surfer's relative motion and orientation at every moment (e.g., depending on the sampling frequency and memory storage limitations and settings) into a global orientation, thereby providing snapshot virtual images of global position and orientation of the surfboard and/or a rendering of the recorded motion of the surfboard in a motion picture format. The application, using such data, could then optionally extrapolate body movements of a surfer from the motion of the surfboard (e.g., using as inputs the length and width of surfboard used, manufacturer of surfboard, model of surfboard, user height, user weight, etc.) and render the body movement of the surfer in a motion picture format. For example, based on a position of and orientation of the surfboard, and velocity of the surfboard, it can be determined if a surfer is riding a wave versus, laying or sitting on the surfboard. The application could also, optionally, extrapolate the changing shape of the wave that was ridden by the surfer from the motion of the surfboard and render the changing shape of the wave in a motion picture format. Thus, the surfer can store, and view, each surf session, reliving each wave of the day (and providing data to show the user's friends just how big or fast that wave really was).

As to the environmental data, the application is configured, at a minimum, to flag or remove fallacious data. Desirably, but optionally, the application uploads valid data to other websites (e.g., NOAA) for analysis. The application itself, or other applications, is advantageously adapted to analyze the uploaded environmental data, such as, by way of example, but not limitation, to geographically interpolate and extrapolate of oceanographic conditions based on the received data from the sensing device(s) 100, provide near-time-forecast oceanographic conditions based on recent environmental data uploads, and/or forecast geographic location and time of optimal water sports experience for a participant based on historical environmental data of the individual user or based on historical environmental data of the other users in the general vicinity of the user (or in another selected area of interest to the user).

In some aspects, the sensing device(s) may be swappable from a first carrier (e.g., surfboard) to a second carrier (e.g., paddle board) or to a third carrier (e.g., sky diving equipment rig) so that a user can obtain sports movement data and environmental data in a plurality of activities.

Accordingly, the web app available to each user of the sensing device(s) provides a user interface for the users water-sport(s) and provides an archive of "videos", virtual renderings of the user's historical water sports sessions, as well as statistics of historical water sports sessions, summaries of uploads of oceanographic data from other users ("Surf Reports"), near-time-forecasts of oceanographic conditions (e.g., as a supplement to conventional surf reports and NOAA forecasts), and may further provide interfaces and links to amateur and professional organizations associated with various water-sports, as well as to private or governmental science or environmental organizations.

Each of these embodiments and obvious variations thereof is contemplated as falling within the spirit and scope of the claimed invention, which is set forth in the following claims. Moreover, the present concepts expressly include any and all combinations and sub-combinations of the preceding elements and aspects. Further, it is contemplated that the present concepts may have applicability to other sporting activities and non-sporting activities other than those noted above, such as atmospheric sports (e.g., skydiving), that do not manipulate the natural environment so as to introduce biases into the measured data (e.g., a nearby vehicle or craft could introduce localized heating). In this regard, the present concepts are applicable to installation on boats, such as, but not limited to sailboats, kayaks, and rowboats.

The invention claimed is:

1. A waterproof device configured to collect environmental data comprising:
   at least one waterproof sensor housing integrated with a device borne by a person or attached to a device borne by a person;
   at least one sensor disposed within the at least one sensor housing, the at least one sensor comprising a GPS unit;
   at least one processor disposed within the at least one sensor housing, the at least one processor being communicatively connected to the at least one sensor;
   at least one physical memory device disposed within the at least one sensor housing, the at least one physical memory device being communicatively connected with the at least one processor;
   at least one switch adapted to change a state of the at least one sensor between at least a first state and a second state, wherein the at least one switch is automatically actuated to cause the state of the at least one sensor to change from the first state to the second state responsive to immersion in water, the first state being an off state and the second state being an on state, wherein, while in the second state, environmental data sensed by the at least one sensor is stored in the at least one physical memory device;
   at least one battery configured to power at least one of the at least one sensor, the at least one processor, or the at least one memory device; and
   a transmitter disposed within the at least one housing, the at least one battery being further configured to power the transmitter,
   wherein the at least one processor is further configured, while the at least one switch is in the second state, to determine whether a location determined by the GPS unit corresponds to a nearshore environment and to cause storage of the environmental data sensed by the at least one sensor in the at least one physical memory device only when the location determined by the GPS unit corresponds to a nearshore environment,
   and
   wherein the environmental data comprises at least one of a direction of a current, a water temperature, a water salinity, a water conductivity, a water pH, or any combination thereof.

2. The waterproof device configured to collect environmental data, in accord with claim 1,
   wherein the at least one switch is adapted to change the state of the at least one sensor between at least the first state and the second state automatically responsive to at least one triggering event, the at least one triggering event comprising at least one of removal from the water, motion above a threshold, or a lack of sufficient motion.

3. The waterproof device configured to collect environmental data, in accord with claim 2,
wherein the at least one switch is operatively associated with a conductivity sensor, and
wherein the at least one triggering event comprises a conductivity change greater than a predetermined threshold.

4. The waterproof device configured to collect environmental data, in accord with claim 2,
wherein the at least one switch is operatively associated with a salinity sensor, and
wherein the at least one triggering event comprises a change in salinity greater than a predetermined threshold.

5. The waterproof device configured to collect environmental data, in accord with claim 4, further comprising a timer, wherein the at least one triggering event comprises both a first triggering event of removal from water and a second triggering event of a lapse of a timer initiated responsive to the removal from water.

6. The waterproof device configured to collect environmental data, in accord with claim 2, further comprising a timer, wherein the at least one triggering event comprises both a first triggering event of removal from water and a second triggering event of a lapse of a timer initiated responsive to the removal from water.

7. The waterproof device configured to collect environmental data, in accord with claim 2, wherein the at least one triggering event comprises a first triggering event of motion above a threshold, and a second triggering event of a lack of sufficient motion.

8. The waterproof device configured to collect environmental data, in accord with claim 1, wherein the at least one waterproof sensor housing is attached to an insulated wetsuit, scuba equipment, personal electronic device, or camera by a tether.

9. The waterproof device configured to collect environmental data, in accord with claim 1,
wherein the at least one sensor comprises at least one water-sports sensor configured to sense movement-based data relating to the water-sports activity, and
wherein the at least one water-sports sensor comprises one or more of a three-axis accelerometer, a three-axis magnetometer, a three-axis gyroscope, or combinations thereof.

10. The waterproof device configured to collect environmental data, in accord with claim 1, wherein the at least one sensor comprises at least one of one or more temperature sensors, one or more water salinity sensors, one or more conductivity sensors, or one or more pH sensors, one or more depth sensors, or any combination thereof.

11. The waterproof device configured to collect environmental data, in accord with claim 1, wherein the environmental data further comprises a barometric pressure.

12. The waterproof device configured to collect environmental data, in accord with claim 1, wherein the environmental data is collected for uploading to a website for analysis.

13. The waterproof device configured to collect environmental data, in accord with claim 1, wherein the transmitter is configured to transmit the environmental data obtained from the at least one sensor, data from the at least one sensor stored in the at least one physical memory device, or both, to an external local device, an external remote device, or both.

14. The waterproof device configured to collect environmental data, in accord with claim 1, wherein the transmitter is configured to transmit the environmental data obtained from the at least one sensor to an external local device via a Bluetooth, spread spectrum frequency-hopping, wifi, xbee, ZigBee, ISA100.11a, WirelessHART, MiWi, or IEEE 802.15 communication protocol.

15. The waterproof device configured to collect environmental data, in accord with claim 1, wherein the transmitter is configured to transmit the environmental data obtained from the at least one sensor to an external remote device comprising a communication device operatively associated with at least one of computer, a server, or a router.

16. The waterproof device configured to collect environmental data, in accord with claim 1, wherein the at least one processor is configured to register connection of the at least one rechargeable battery to a power source and, responsive thereto, is further configured to automatically communicatively provide a means by which an external communication device can connect and initiate data transfer of the environmental data from the waterproof device's at least one physical memory device.

17. The waterproof device configured to collect environmental data, in accord with claim 1, further comprising an external I/O port.

18. The waterproof device configured to collect environmental data, in accord with claim 1, wherein the environmental data comprises at least two or more of an air temperature, a wind velocity, a wind direction, a current direction, a wave direction, a water temperature, a wave height, a water salinity, a water conductivity, or a water pH.

* * * * *